United States Patent [19]

Ogawa et al.

[11] Patent Number: 5,716,958
[45] Date of Patent: Feb. 10, 1998

[54] AMINO ACID DERIVATIVE HAVING ANTI-CCK ACTIVITY

[75] Inventors: Masashi Ogawa, Inagi; Tadashi Morita, Hamura; Kiyoshi Matsuda, Kokubunji; Norihiro Iibuchi, Hamura; Shinpei Kidokoro, Tokyo, all of Japan

[73] Assignee: Tobishi Pharmaceutical Co., Ltd., Tokyo, Japan

[21] Appl. No.: 513,018

[22] Filed: Aug. 9, 1995

[30] Foreign Application Priority Data

Oct. 27, 1994 [JP] Japan .................................. 6-286138
Dec. 19, 1994 [JP] Japan .................................. 6-333776

[51] Int. Cl.$^6$ ............. A61K 31/495; A61K 31/445; C07D 401/14
[52] U.S. Cl. ............ 514/253; 514/80; 514/318; 514/323; 544/337; 544/364; 544/366; 544/369; 544/357; 544/373; 544/408; 546/21; 546/194; 546/201
[58] Field of Search ................. 544/364, 366, 544/369, 373, 337, 357, 408; 546/194, 201, 21; 514/253, 318, 323, 80

[56] References Cited

U.S. PATENT DOCUMENTS

| | | | |
|---|---|---|---|
| 4,769,389 | 9/1988 | Makovec et al. | 514/563 |
| 4,791,215 | 12/1988 | Rovati et al. | 558/415 |
| 4,826,878 | 5/1989 | Makovec et al. | 514/561 |
| 4,891,381 | 1/1990 | Makovec et al. | 514/119 |
| 4,891,383 | 1/1990 | Makovec et al. | 514/443 |
| 4,895,866 | 1/1990 | Fenske et al. | 514/392 |
| 5,064,853 | 11/1991 | Gasc et al. | 514/419 |
| 5,130,474 | 7/1992 | Makovec et al. | 562/448 |
| 5,248,679 | 9/1993 | Sato et al. | 514/220 |
| 5,346,907 | 9/1994 | Kerwin | 514/312 |
| 5,391,547 | 2/1995 | Makovec et al. | 514/563 |
| 5,401,737 | 3/1995 | Sato et al. | 514/220 |

FOREIGN PATENT DOCUMENTS

| | | |
|---|---|---|
| 0383690 | 8/1990 | European Pat. Off. . |
| 8805774 | 8/1988 | WIPO . |
| 8902431 | 3/1989 | WIPO . |

OTHER PUBLICATIONS

Woodruff et al, *Neuropeptides*, 19, pp. 45–56 (1991).
Murayama et al, *Pancreas* 5, pp. 439–444 (1990).
Funakoshi et al, *Gastroenterologia Japonica* 27, pp. 78–82 (1992).
Tani et al, *Pancreas*, 5, pp. 284–290 (1990).
Tani et al, *Pancreas*, 8, pp. 109–115 (1993).
Setnikar et al. *Arzneim–Forsch./Drug Res.* 37, pp. 1172–1174 (1987).
Woodruff et al. *Annu. Rev. Pharmacol. Toxicol.* 31, pp. 469–501 (1991).
Morimoto et al, Abstract for *Journal of Surgical Oncology* 53, p. 47 (1993).
Shivaram et al. Abstract for *Journal of Surgical Research* 53 p. 234 (1992).

*Primary Examiner*—Emily Bernhardt
*Attorney, Agent, or Firm*—Ladas & Parry

[57] ABSTRACT

A compound represented by the formula (1):

$$\begin{array}{c}R_1\\ \phantom{R}\diagdown\\ \phantom{RR}CH-A\phantom{XX}N-C-CH-NH-C-R_3\\ \phantom{R}\diagup\phantom{XXXXXX}\|\phantom{X}|\phantom{XXXX}\|\\ R_1\phantom{XXXXXXX}O\phantom{X}(CH_2)_m\phantom{X}O\\ \phantom{XXXXXXXXXXXX}|\\ \phantom{XXXXXXXXXXXX}(S)_n\\ \phantom{XXXXXXXXXXXX}|\\ \phantom{XXXXXXXXXXXX}R_2\end{array}\tag{1}$$

wherein, m is an integer of 1 to 3;

n is an integer 0 or 1;

A represents CH or N atom, and forms together with the N atom bonded to the carbonyl group a piperidine ring or a piperazine ring;

$R_1$ independently represents a straight or branched chain alkyl group having 1 to 4 carbon atoms; a cycloalkyl group having 3 to 8 carbon atoms; a phenyl group, unsubstituted or substituted with a halogen atom or with an alkoxy group having 1 to 4 carbon atoms; or a pyridyl group; or two $R_1$, together with the group >CH— to which they bind, form a dibenzo cycloheptenyl group or a fluorenyl group;

$R_2$ represents a phenyl group substituted with a carboxyl or substituted carboxyl group; a pyridyl group substituted with a carboxyl or substituted carboxyl group, a pyrazyl group substituted with a carboxyl or substituted carboxyl group, an oxazolyl substituted with a carboxyl or substituted carboxyl group, a triazolyl substituted with one or two carboxyl or substituted carboxyl groups, or a phosphonopyridyl group; and $R_3$ represents an indolyl group unsubstituted or substituted with a substituent selected from the group consisting of a halogen atom, a hydroxy group, an alkoxy group having 1 to 4 carbon atoms and methoxycarbonyl ethyl group and the pharmaceutically acceptable salts thereof.

12 Claims, No Drawings

AMINO ACID DERIVATIVE HAVING ANTI-CCK ACTIVITY

BACKGROUND OF THE INVENTION

1. Field of the Invention

The present invention relates to a compound that is a derivative of serine, aspartic acid and glutamic acid, and more particularly, to a compound having a powerful and selective competitive inhibitory activity on cholecystokinin (CCK) receptors.

2. Related Art

CCK is a peptide digestive tract hormone that is released, into the blood, from the mucoepithelium of the duodenum due to the degradation products of proteins and fats contained in food. It is known to demonstrate physiological action including contraction of the gall bladder and stimulation of secretion of pancreatic enzymes as a result of binding with receptors. It has become clear that CCK also exists in the brain and other components of the central nervous system. CCK has thus become known as a cerebrointestinal peptide hormone that has the action of a neurotransmitter as well as the action of a digestive tract hormone. Examples of its action that have been reported include promotion of extrapancreatic secretions, promotion of gall bladder contraction, promotion of intestinal peristalsis, inhibition of small intestine absorption and increased gastric acid secretion. Peptides such as CCK58, CCK39, CCK33 and CCK8 can be isolated from tissue. The structures of these peptides have features in common with the four C-terminal amino acid residues of gastrin, another digestive tract hormone.

Recently, the existence of a peripheral receptor in the form of CCK-A and a central receptor in the form of CCK-B has been clarified as a result of research relating to CCK and CCK receptors. Various physiological activities have been reported with respect to substances that competitively inhibit these receptors. For example, substances that competitively inhibit CCK-A receptors are known to have actions that inhibit extrapancreatic secretions, actions that inhibit gall bladder contraction, actions that promote gastric discharge and actions that inhibits intestinal movement, while substances that competitively inhibit CCK-B receptors are known to have anti-ulcer actions. Thus, substances that competitively inhibit CCK receptors may be useful in the treatment of diseases such as pancreatitis, pancreatic cancer, digestive ulcers, gall bladder dysfunction and colitis (Japanese Unexamined Patent Publication No. 62-181246, Japanese Unexamined Patent Publication No. 63-201156, Japanese Unexamined Patent Publication No. 2-111774 and so forth). In particular, since these substances have the important action of stimulating secretion of pancreatic enzymes with respect to the pancreas, there is a strong possibility that CCK mediates bonding with receptors as one of the factors of the occurrence and development of acute pancreatitis. As such, agents that competitively inhibit CCK receptors are predicted to be useful in the treatment of pancreatitis. Based on this background, numerous compounds have been reported that specifically and competitively inhibit CCK receptors, and their clinical application has attracted considerable attention. For example, glutamic acid derivative CR-1505 (Loxiglumide, Japanese Unexamined Patent Publication No. 62-181246) and benzodiazepine derivative FK-480 (Japanese Unexamined Patent Publication No. 2-111774), which are both substances that competitively inhibit CCK-A receptors, are considered to be useful as pancreatitis therapeutic drugs.

SUMMARY OF INVENTION

The object of the present invention is to provide a serine, aspartic acid or glutamic acid derivative having strong inhibitory activity with respect to CCK and an action that selectively and competitively inhibits CCK-A receptors. Namely, the object of the present invention is to provide a serine, aspartic acid or glutamic acid derivative that is effective as a competitive inhibitor of CCK receptors in the form of a pharmaceutical product that has useful and novel action with respect to the prevention and treatment of pancreatitis, pancreatic cancer, duodenal ulcers, gastric ulcers, digestive ulcers, colitis, gall bladder dysfunction and so forth.

Accordingly, the present invention provides an amino acid derivative represented by the following formula (1):

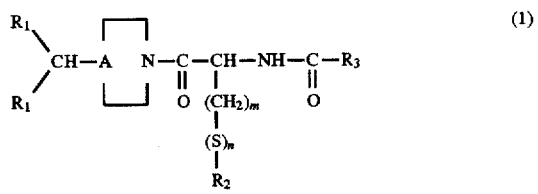

wherein, m is an integer of 1 to 3;

n is an integer 0 or 1;

A represents CH or N atom, and forms together with the N atom bonded to the carbonyl group a piperidine ring or a piperazine ring;

$R_1$ independently represents a straight or branched chain alkyl group having 1 to 4 carbon atoms; a cycloalkyl group having 3 to 8 carbon atoms; a phenyl group, unsubstituted or substituted with a halogen atom or with an alkoxy group having 1 to 4 carbon atoms; or a pyridyl group; or two $R_1$, together with the group >CH— to which they bind, form a dibenzo cycloheptenyl group or a fluorenyl group;

$R_2$ represents a phenyl group substituted with a carboxyl or substituted carboxyl group; a pyridyl group substituted with a carboxyl or substituted carboxyl group, a pyrazyl group substituted with a carboxyl or substituted carboxyl group, an oxazolyl substituted with a carboxyl or substituted carboxyl group, a triazolyl substituted with one or two carboxyl or substituted carboxyl groups, or a phosphonopyridyl group; and $R_3$ represents an indolyl group unsubstituted or substituted with a substituent selected from the group consisting of a halogen atom, a hydroxy group, an alkoxy group having 1 to 4 carbon atoms and a methoxycarbonyl ethyl group; and pharmaceutically acceptable salts thereof.

DETAILED DESCRIPTION

The compound of the above-mentioned general formula (1) is a derivative of serine indicated in the following formula (2):

aspartic acid indicated in the following formula (3):

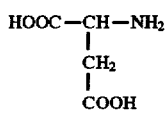

or glutamic acid indicated in the following formula (4):

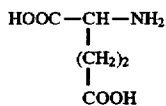

Thus, the basic skeleton of the compound of general formula (1) is represented with the following general formula:

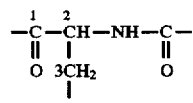

Since the compound of the present invention has an asymmetric carbon atom at the second position in its basic skeleton, it is obtained in the form of a racemic compound or enantiomer.

In the case where A is CH in the above-mentioned general formula (1), A together with the N represents a piperidine ring. Alternatively, in the case where A is an N atom, A together with the N represents a piperazine ring. These rings compose the following groups:

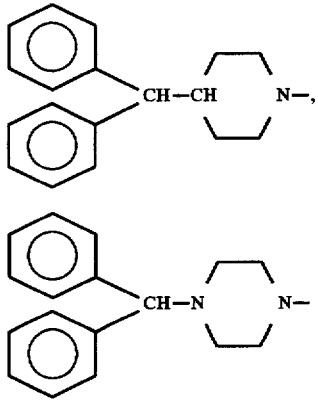

in the case where $R_1$ is a phenyl group. These groups are particularly preferable in terms of the object of the present invention.

Other than the above-mentioned phenyl group, $R_1$ is preferably a straight or branched chain alkyl group having 1 to 4 carbon atoms such as a butyl group or isopropyl group, or a cycloalkyl group such as a cyclohexyl group. An example of a substituted phenyl group is a phenyl group substituted with a halogen atom or an alkoxy group having 1 to 4 carbon atoms, and preferably a phenyl group substituted with a fluorine atom or methoxy group. A pyridyl group may be substituted. The dibenzo[a,d]cycloheptenyl group or fluorenyl group may be substituted. Examples of starting materials having these groups are indicated in the production examples described later.

In one embodiment of the present invention, $R_2$ is a group linked to the thio group (—S—) converted from the —OH group of serine. The β-carboxyl group of aspartic acid and the γ-carboxyl group of glutamic acid may be also converted to —$CH_2OH$ groups by reduction, and this OH group can be converted to a thio group (—S—) in the same manner as the OH group of serine.

In another embodiment of the present invention, the terminal hydroxy group of serine is replaced by being involved in the formation of a triazolyl group, which is one example of $R_2$. The β-carboxyl group of aspartic acid and the γ-carboxyl group of glutamic acid are converted into —$CH_2OH$ groups by reduction, and this hydroxy group is replaced by being involved in the formation of a triazolyl group in the same manner as the hydroxy group of serine. In this case, since one —$CH_2$— group is added, m of the compound of formula (1) derived from aspartic acid is 2, and m of the compound of formula (1) derived from glutamic acid is 3. In addition, in the case of compounds wherein m is 2 or 3, the compounds are derivatives of aspartic acid or glutamic acid wherein the above-mentioned hydroxy group is replaced with a carboxypyridylthio group.

As a result of the β and γ-carboxyl groups of aspartic acid and glutamic acid being converted into 4-methoxycarbonyloxazol-5-yl groups by direct reaction with methyl isocyanoacetate, they are converted into an carboxyoxazolyl group, which is one example of the $R_2$ group. In this case in the resulting compound of formula (1) derived from aspartic acid or glutamic acid, m is 1 or 2 respectively.

According to one embodiment of the present invention, $R_3$ is an indolyl group, and particularly an indole-2-yl group. Examples of substituent groups of the indolyl group include a halogen atom, a hydroxy group, an alkoxy group having 1 to 4 carbon atoms and a methoxycarbonyl ethyl group. The halogen atom is preferably a chlorine atom, while the alkoxy group is preferably a methoxy group.

According to one embodiment of the present invention, in formula (1), m is 1, n is 1, and A, $R_1$, $R_2$ and $R_3$ are as shown below.

TABLE 1

| Compound No. | Isomer RS | A | $R_1$ | $R_2$ | $R_3$ |
|---|---|---|---|---|---|
| 1-6 | R | N | (phenyl) | HOOC-pyridyl | indolyl (NH) |
| 2-6 | R | CH | same as above | same as above | same as above |

TABLE 1-continued

| Compound No. | Isomer RS | A | R₁ | R₂ | R₃ |
|---|---|---|---|---|---|
| 3-2 | R | N | same as above | same as above | 5-chloroindol-2-yl |
| 4 | R | N | same as above | 2-methyl-3-(methoxycarbonylethoxycarbonyl)pyridin-? | indol-2-yl |
| 5 | R | N | same as above | 2-methyl-3-carboxypyridin-? | 1-(2-methoxycarbonylethyl)indol-2-yl |
| 6-2 | R | N | same as above | same as above | 5-methoxyindol-2-yl |
| 7-4 | R | N | 4-methoxyphenyl | same as above | indol-2-yl |
| 8-5 | R | N | pyridin-2-yl | 2-methyl-3-carboxypyridin-? | indol-2-yl |
| 9-3 | R | N | phenyl | 2-methyl-3-carboxyphenyl | same as above |
| 10-4 | R | N | 4-fluorophenyl | 2-methyl-3-carboxypyridin-? | same as above |
| 11-4 | S | N | phenyl | same as above | same as above |
| 12-2 | R | N | same as above | same as above | 5-hydroxyindol-2-yl |

TABLE 1-continued

| Compound No. | Isomer RS | A | R₁ | R₂ | R₃ |
|---|---|---|---|---|---|
| 13-4 | R | N | CH₃— | same as above | (indole) |
| 14-5 | R | N | C₄H₉— | same as above | same as above |
| 15-4 | R | N | (CH₃)₂CH— | same as above | same as above |
| 16-5 | R | N | (cyclohexyl) | HOOC-pyridyl | (indole) |
| 17-3 | R | N | (phenyl) | HOOC-pyrazinyl | same as above |
| 18-5 | R | N | (diphenylmethyl) | HOOC-pyridyl | same as above |
| 19-5 | R | N | (dibenzosuberyl) | same as above | same as above |
| 20-2 | R | CH | (phenyl) | same as above | (5-Cl-indole) |
| 21-2 | R | CH | same as above | same as above | (5-OCH₃-indole) |
| 22-4 | R | N | same as above | PO(OH)₂-pyridyl | (indole) |
| 1-5 | R | N | same as above | CH₃OOC-pyridyl | same as above |

(5) of Example 1

According to another embodiment of the present invention, A is an N atom, R1 is a phenyl group, n is 0, R₃ is:

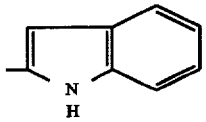

and m and R2 are as indicated below.

| Compound No. | Isomer R,S | m | R$_2$ |
|---|---|---|---|
| 23-6 | S | 3 | 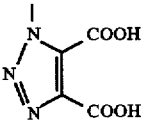 |
| 24-3 | S | 2 | 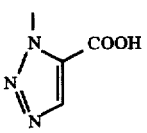 |
| 25-7 | S | 2 | 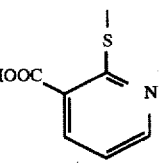 |
| 26-5 | S | 2 | 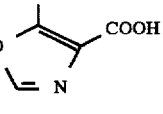 |
| 27-5 | S | 1 | Same as above |
| 28-3 | S | 3 | 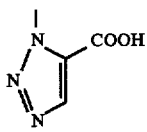 |
| 29-2 | S | 3 | 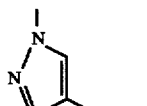 |
| 30-4 | S | 1 | Same as above |
| 31-3 | S | 1 | 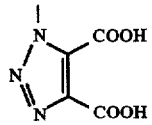 |
| 32-2 | S | 1 | 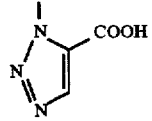 |

In producing the compound of the present invention, N-t-butoxycarbonyl-O-tetrahydropyranyl-L-serine, represented by the following formula:

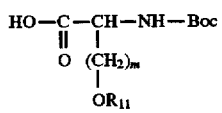  (5)

(wherein Boc represents a t-butoxycarbonyl group, R$_{11}$ represents a tetrahydropyranyl group, and m represents an integer of 1), is used as a serine derivative for the starting compound.

N-t-butoxycarbonyl-L-aspartate β-benzylester (m represents an integer of 1 in formula (6)) and N-t-butoxycarbonyl-L-glutamate γ-benzylester (m represents an integer of 2 in formula (6)) are used for the aspartic acid and glutamic acid derivatives used as starting compounds respectively. These compounds are commercially available.

  (6)

(wherein Bz represents a benzyl group and m is an integer of 1 or 2).

1. α-Carboxyl Group Amidation Step (Step 1)

The compounds of the above-mentioned formula (5) or formula (6) are reacted with the compound represented with the following formula (7):

  (7)

(wherein A and R$_1$ are the same as A and R$_1$ in the compound of formula (1)) to obtain a compound represented by the following formula (8):

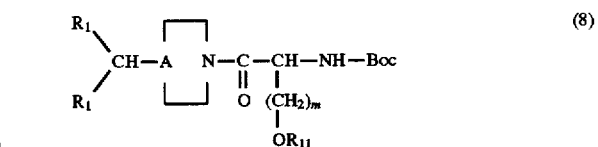  (8)

(wherein R$_{11}$ represents a tetrahydropyranyl group and n is an integer of 1), or a compound represented with the following formula (9):

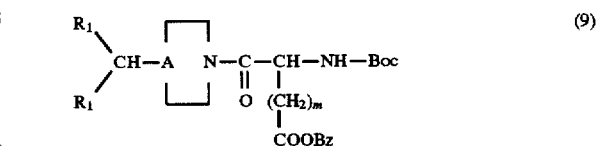  (9)

(wherein Bz represents a benzyl group and m is an integer of 1 or 2).

Namely, compound (8) is a compound derived from serine, and compound (9) is either a compound derived from aspartic acid in the case m=1 or a compound derived from glutamic acid in the case m=2.

2. Modification of Terminal Hydroxy Group, β-Carboxyl Group and γ-Carboxyl Group (Step 2)

(1) When the compound of formula (8) is hydrolyzed, —OR$_{11}$ is converted to an —OH group so as to form a compound represented by the formula (10) wherein m is the integer 1.

(2) When the compound of formula (9) is reduced, the —COOBz group is converted to a —CH$_2$OH group. Thus, the resulting compound is a compound having the general formula represented by the following formula (10):

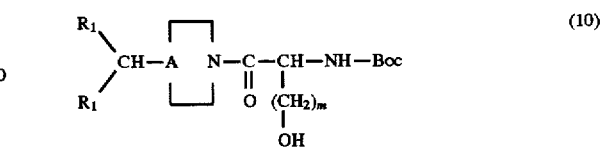  (10)

(wherein m represents an integer 2 or 3).

(3) When the compound of formula (9) is hydrolyzed, the compound is obtained represented by the following formula (11):

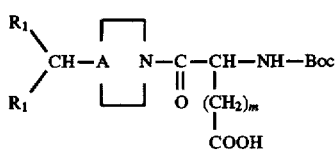

(wherein m represents an integer 1 or 2).

Step 2-(1)

Introduction of a Carboxy-Substituted Triazolyl Group or Carboxypyridylthio Group for the Terminal Hydroxy Group of Formula (10) The compound of the following formula (12):

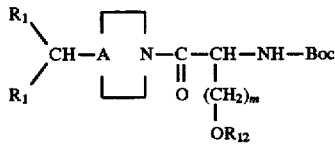

(wherein m represents an integer of 1 to 3, and $R_{12}$ represents a mesyl group or tosyl group) is formed by reacting the compound of formula (10) with methanesulfonyl chloride or para-toluenesulfonyl chloride.

The compound represented by the following formula (13):

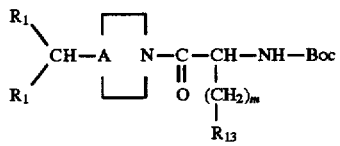

(wherein m represents an integer of 1 to 3 and $R_{13}$ represents an azide group) is formed when the compound of formula (12) is reacted with sodium azide.

The compound represented by the following formula (14):

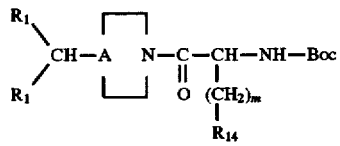

(wherein m represents an integer of 1 to 3, and $R_{14}$ represents a methoxycarbonyltriazolyl group) is acquired when the compound of formula (13) is reacted with dimethyl acetylenedicarboxylate or methyl propiolate.

The compound represented by the following formula (15):

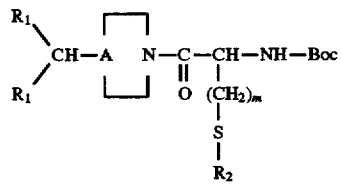

(wherein, $R_2$ is the same as $R_2$ of formula (1)) is acquired when the compound represented with formula (12) is reacted with the compound represented by the following formula:

(wherein, $R_2$ is the same as $R_2$ of the compound of formula (1)).

The alkoxycarbonyl group of groups $R_{14}$ and $R_2$ in the compounds of the above-mentioned formula (14) and (15) may be converted to a carboxyl group by, for example, hydrolysis in the final step.

Step 2-(2)

Modification of β-Carboxyl Group or γ-Carboxyl Group of the Compound of Formula (11) The compound represented by the following formula (16):

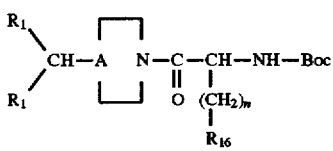

(wherein, n represents an integer or 1 or 2 and $R_{16}$ represents the following group):

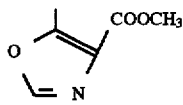

is obtained by reacting methyl isocyanoacetate with the compound of formula (11).

When the three types of compounds of the above-mentioned formula (14), formula (15) and formula (16) are combined, they can be represented by the following formula (17):

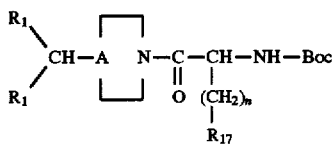

(wherein, n represents an integer of 1 to 3 and R17 represents $R_{14}$, —S—$R_2$ or $R_{16}$).

3. Amino Group Acylation with an Indolylcarbonyl Group (Step 3)

The compound of formula (17) is converted into the compound represented by the following formula (18):

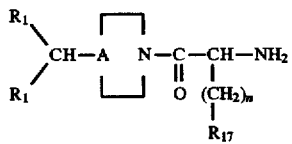

(wherein, n represents an integer of 1 to 3 and $R_{17}$ represents $R_{14}$, —S—$R_2$ or $R_{16}$) by eliminating its t-butoxycarbonyl group.

The compound represented by the following formula (19):

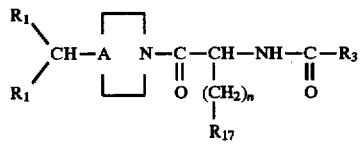

(wherein, n represents an integer from 1 to 3, $R_{17}$ represents $R_{14}$, —S—$R_2$ or $R_{16}$, and $R_3$ represents an indolyl group) can be acquired by reacting the indole carboxylic acid or its reactive derivative represented by the formula $R_3COOH$ (wherein, $R_3$ represents an unsubstituted or substituted indolyl group) with the compound of formula (18).

As previously mentioned, with respect to group $R_{17}$, since $R_{14}$ represents a methoxycarbonyltriazolyl group, $R_2$ of —S—$R_2$ represents, for example, an alkoxycarbonylpyridin-2-yl group, and $R_{16}$ represents a methoxycarbonyloxazolyl group, $R_{14}$ is converted to a carboxytriazolyl group and $R_{16}$ is converted to a carboxyoxazolyl group by hydrolyzing the compound of formula (19), thus enabling the compound of formula (1) of the present invention to be derived.

The following provides an explanation of the reaction conditions of each of the above-mentioned steps.

Step 1

The compound of formula (8) is obtained by condensing the compound of formula (5) and the compound of formula (7). Examples of condensation agents used include 1-ethyl-3-(3-dimethylaminopropyl)carbodiimide hydrochloride or dicyclohexylcarbodiimide. 1-Hydroxybenztriazole (HOBT) is suitable used as adjuvant. Examples of solvents used include tetrahydrofuran, ethyl acetate, acetonitrile, dimethoxyethane, dimethylformamide and dichloromethane. Although the reaction temperature is preferably −10° to 30° C., and the reaction time is preferably from 30 minutes to 20 hours, the temperature and time are not limited to these.

The compound of formula (9) is acquired by condensing the compound of formula (6) and the compound of formula (7) under similar reaction conditions.

Step 2

Preliminary Treatment for Step 2

(1) The compound of formula (8) is hydrolyzed under acidic conditions to remove the protective group of the —OH group to obtain the compound of formula (10) (wherein m=1) (alcohol form). The target compound is easily obtained by, for example, adding 1N aqueous hydrochloric acid in tetrahydrofuran and stirring for the hydrolysis conditions.

(2) The compound of formula (9) is reduced to the compound of formula (10) (wherein m is 2 or 3) (alcohol form) by heating and refluxing this compound with sodium borohydride in, for example, ethanol.

The compound of formula (11) may also be converted into the alcohol compound of formula (10) wherein m is 2 or 3 by obtaining the N-succimidoxy form by reacting with disuccineimidyl oxalate and then reducing with sodium borohydride.

(3) Hydrolysis of the benzylester portion of the compound of formula (9) yields the corresponding carboxylic acid of formula (11) by reacting in tetrahydrofuran, methanol, water or a mixed solvent of these using lithium hydroxide.

Step (2)-1

The compound of formula (10) is converted into the corresponding compound of formula (12) by reacting with a sulfonyl halide such as methanesulfonyl chloride or para-toluenesulfonyl chloride in the presence of a base. Examples of solvents used in this reaction include dichloromethane, chloroform, tetrahydrofuran, dioxane, ethyl acetate, dimethylformamide and mixtures of these. In addition, examples of bases that can be used include tertiary amines such as triethylamine, pyridine, diisopropylethylamine and N,N-diethylaniline or inorganic bases such as potassium carbonate. The reaction temperature is −20° to 50° C., and preferably in the vicinity of −10° C.

The compound of formula (13) is acquired by reacting the compound of formula (12) with sodium azide in the presence of N,N'-dimethylimidazolidinone.

The compound of formula (14) is acquired by reacting the compound of formula (13) while heating and refluxing with dimethyl acetylenedicarboxylate or methyl propiolate in a solvent such as 1,2-dichloroethane.

For the introduction of the carboxypyridylthio group, the compound of formula (15) is acquired by reacting a thiol (HS—$R_2$) such as 2-mercaptobenzoic acid, 2-mercaptonicotinate or 2-methoxycarbonyl-3-mercaptopyrazine with the compound of formula (12) in a reaction solvent. Examples of reaction solvents used include dimethylformamide, dimethylsulfoxide, N,N'-dimethylimidazolidinone, tetrahydrofuran, ethyl acetate, dichloromethane and acetonitrile. A base such as potassium carbonate or triethylamine may also be used as necessary.

Step 2-(2)

When methyl isocyanoacetate is reacted with the carboxylic acid of the compound of formula (11), the corresponding oxazole ring is formed. For example, the compound of formula (16), in which the carboxyl group is replaced with a oxazolyl group, is obtained by reacting methyl isocyanoacetate, diphenylphosphoryl azide and potassium carbonate with carboxylic acid in a dimethylformamide solvent.

Step 3

Preliminary Step

The Boc (t-butoxycarbonyl) group of the compound of formula (17) can be easily eliminated by acid treating with trifluoroacetic acid or hydrogen chloride/ethyl acetate to obtain the corresponding amino form of the compound of formula (18).

Indoly Group Introduction Step

By condensing the compound of formula (18) with unsubstituted or substituted indole-2-carboxylic acid or its reactive acid derivative, the corresponding amide form of the compound of formula (19), namely the compound of the present invention, is obtained. The reaction conditions are similar to those of Step 1 previously described.

EXAMPLES

The following indicates Examples of the compound of the present invention, although the present invention is not limited thereto.

Starting Material Production Example 1:

1-bis(4-methoxyphenyl)methylpiperazine (1) Bis(4-methoxyphenyl)methanol 1.03 g of sodium borohydride was added to 4.84 g of 4,4'-dimethoxybenzophenone in 80 ml of ethanol, followed by stirring for 7 hours at room temperature. Next, after adding water and stirring for 30 minutes, the solution was concentrated to roughly 20 ml. Moreover, ethyl acetate and water were added and after extracting with ethyl acetate (50 ml×3), the product was washed with saturated brine and dried with anhydrous sodium sulfate. The solvent was distilled off under reduced pressure to obtain 4.84 g of the target compound. Yield: 99%

NMR (CDCl$_3$) δ: 2.30(1H,bs), 3.76(6H,s), 5.74(1H,bs), 6.85(4H,d,J=6.6 Hz), 7.26(4H,d,J=6.6 Hz)

(2) 1-Formyl-4-bis(4-methoxyphenyl)methylpiperazine 1.22 g of the above-mentioned compound (1) and 1.01 g of triethylamine were dissolved in 15 ml of dichloromethane. 5 ml of a dichloromethane solution containing 630 mg of methanesulfonyl chloride was then dropped thereon over a period of 10 minutes, at −15° C. After stirring for 30 minutes at the same temperature, 5 ml of a dichloromethane solution containing 1.14 g of N-formylpiperazine was dropped thereon into the first solution, over a period of 10 minutes, followed by stirring for 1 hour at −5° C. The reaction solution was made alkaline by the addition of saturated sodium bicarbonate solution and then was extracted with dichloromethane (10 ml×3). Next, after washing with saturated brine, the reaction solution was dried with anhydrous sodium sulfate. The solvent was then distilled off under reduced pressure to obtain 1.80 g of residue. This was then purified with silica gel column chromatography (elution solvent: ethyl acetate) to obtain 1.68 g of the target compound. Yield: 98%

NMR (CDCl$_3$) δ: 2.3–2.4(4H,m), 3.34(2H,bt), 3.52(2H, bt), 3.75(6H,s), 4.19(1H,s), 6.82(4H,d,J=6.6 Hz), 7.29(4H, d,J=6.6 Hz), 7.98(1H,s)

(3) 1-bis(4-methoxyphenyl)methylpiperazine 6 ml of tetrahydrofuran, 9 ml of methanol and 9 ml of 10% aqueous sodium hydroxide were added to 1.68 g of the above-mentioned compound (2) followed by stirring for 2 hours at 60° C. After concentrating the reaction solution to roughly 10 ml and saturating it with sodium chloride, the concentrate was extracted with dichloromethane (20 ml×4). After drying with anhydrous sodium sulfate, the solvent was distilled off under reduced pressure to obtain 1.48 g of the target compound. Yield: 95%

NMR (CDCl$_3$) δ: 1.48(1H,bs), 2.32(4H,bt), 2.86(4H,t, J=4.9 Hz), 3.75(6H,s), 4.12(1H,s), 6.80(4H,d,J=6.6 Hz), 7.31(4H,d,J=6.6 Hz)

The following compounds were produced using similar methods.

1. 1-Isopropylpiperazine

NMR (CDCl$_3$) δ: 1.04(6H,d,J=6.6 Hz), 1.62 (1H,bs), 2.52 (4H,bt), 2.62(1H,sep,J=6.6 Hz), 2.90(4H,bt)

2. 1-Bis(2-pyridyl)methylpiperazine

NMR (CDCl$_3$) δ: 2.3–2.5(4H,m), 2.52(1H,bs), 2.8–3.0 (4H,m), 4.65(1H,s), 7.0–7.2(2H,m), 7.5–7.7(4H,m), 8.4–8.6 (2H,m)

3. 1-(1-Butylpentyl)piperazine

NMR (CDCl$_3$) δ: 0.8–1.0(6H,m), 1.2–1.6(12H,m), 1.65 (1H,bs), 2.2–2.3(1H,m), 2.4–2.6(4H,m), 2.8–3.0(4H,m)

4. 1-Bis(4-fluorophenyl)methylpiperazine

NMR (CDCl$_3$) δ: 0.63(1H,s), 2.1–2.5(4H,m), 2.7–3.0 (4H,m), 4.20(1H,s), 6.8–7.1(4H,m), 7.2–7.4(4H,m)

5. 1-Diisopropylmethylpiperazine

NMR (CDCl$_3$) δ: 0.8–1.0(12H,m), 1.60(1H,bs), 1.8–2.0 (3H,m), 2.4–2.6(4H,m), 2.7–2.9(4H,m)

6. 1-Dicyclohexylmethylpiperazine

NMR (CDCl$_3$) δ: 0.9–1.4(11H,m), 1.5–1.8(12H,m), 1.8–2.0 (1H,m), 2.6–2.8(4H,m), 2.8–3.0(4H,m)

7. 1-(9-Fluorenyl)piperazine

NMR (CDCl$_3$) δ: 1.46(1H,bs), 2.62(4H,dd,J=5.0 Hz, 4.3 Hz), 2.84(4H,dd,J=5.0 Hz, 4.3 Hz), 4.80(1H,s), 7.2–7.4 (4H,m), 7.6–7.7(4H,m)

8. 1-(10,11-Dihydro-5H-dibenzo[a,d]cyclohepten-5-yl) piperazine

NMR (CDCl$_3$) δ: 1.70(1H,bs), 2.1–2.3(4H,m), 2.7–2.9 (6H,m), 3.94(1H,s), 3.9–4.1(2H,m), 7.9–8.2(8H,m)

Starting Material Production Example 2

Ethyl 2-mercaptonicotinate (1) Ethyl 2-chloronicotinate 25.7 g of 2-chloronicotinic acid was dissolved in 350 ml of dimethylformamide followed by the addition of 23.6 g of potassium carbonate and 15.8 ml of ethyl iodide and the solution was stirred for 18 hours at room temperature. Water was added to the reaction solution followed by extraction with ethyl acetate (200 ml×3). After washing with water and saturated brine, the reaction solution was dried with anhydrous sodium sulfate. After distilling off the solvent under reduced pressure, the residue was purified with silica gel column chromatography (elution solvent: hexane/ethyl acetate=1/1) to obtain 29.7 g of the target compound. Yield: 98%

NMR (CDCl$_3$) δ: 1.42(3H,t,J=7.1 Hz), 4.41(2H,q,J=7.1 Hz), 7.35(1H,dd,J=7.5 Hz, 5.9 Hz), 8.16(1H,dd,J=7.5 Hz, 1.7 Hz), 8.52(1H,dd,J=5.9 Hz, 1.7 Hz)

(2) Ethyl 2-mercaptonicotinate 250 ml of ethanol was added to 55.9 g of sodium sulfide 9-hydrate and 59.7 g of sulfur powder and refluxed while heating for 1.5 hours. 28.8 g of ethyl 2-chloronicotinate in 40 ml of ethanol was added to this solution followed by stirring for 4 hours at 70° C. After cooling to room temperature, the reaction solution was added to 240 ml of 2N aqueous hydrochloric acid cooled with ice. After adjusting to pH 6 with sodium bicarbonate, the insoluble matter was filtered out. After concentrating the filtrate to roughly 250 ml and saturating with sodium chloride, the filtrate was extracted with dichloromethane/ethanol=9/1 (100 ml×3). After washing with saturated brine, the reaction solution was dried with anhydrous sodium sulfate followed by distilling off the solvent under reduced pressure to obtain 22.4 g of the target compound. Yield: 79%

NMR (CDCl$_3$) δ: 1.41(3H,t,J=7.1 Hz), 4.42(2H,q,J=7.1 Hz), 6.89(1H,dd,J=7.5 Hz, 5.9 Hz), 7.89(1H,dd,J=5.9 Hz, J=1.7 Hz), 7.96(1H,dd,J=7.5 Hz, 1.7 Hz)

Starting Material Production Example 3

N-t-butoxycarbonyl-O-tetrahydropyranyl-L-serine 7.65 g of N-t-butoxycarbonyl-L-serine and 3.88 g of 3,4-dihydro-2H-pyrane were dissolved in 60 ml of dichloromethane followed by the addition of 0.47 g of pyridinium p-toluene sulfonate and the solution was stirred for 3 hours at room temperature. After the reaction solution was washed with water and saturated brine, the solvent was distilled off under reduced pressure to obtain 9.90 g of the target compound. Yield: 92%

Example 1

(1) (S)-4-diphenylmethyl-1-(3-hydroxy-2-t-butoxycarbonylamino)propionylpiperazine 2.89 g of N-t-butoxycarbonyl-O-tetrahydropyranyl-L-serine, 2.52 g of 1-benzhydrylpiperazine and 1.53 g of 1-hydroxybenzotriazole hydrate were dissolved in 30 ml of dichloromethane followed by the addition of 1.92 g of 1-ethyl-3-(3'-dimethylaminopropyl)carbodiimide hydrochloride and the solution was stirred for 14 hours at room temperature. After washing the reaction solution with saturated sodium bicarbonate and saturated brine, and drying with anhydrous sodium sulfate, the solvent was distilled off under reduced pressure to obtain 4.98 g of residue. 20 ml of tetrahydrofuran and 30 ml of 1N hydrochloric acid were added to this residue followed by stirring for 1 hour at room temperature. The reaction solution was then made alkaline by addition of saturated sodium bicarbonate followed by extraction with ethyl acetate (50 ml×3) and was washed with saturated brine. After drying with anhydrous sodium sulfate, the solvent was distilled off under reduced pressure to obtain 4.56 g of residue. This was then purified with silica gel column chromatography (elution solvent: hexane/ethyl acetate=1/1) to obtain 2.31 g of target compound (1-1). Yield: 53%

NMR (CDCl$_3$) δ: 1.42(9H,s), 2.3–2.5(4H,m), 3.4–3.8(7H, m), 4.24(1H,s), 4.5–4.7(1H,m), 5.72(1H,bd), 7.1–7.3(6H, m), 7.3–7.5(4H,m)

(2) (S)-4-diphenylmethyl-1-(3-mesyloxy-2-t-butoxycarbonylamino)propionylpiperazine 15 ml of dichloromethane was added to 2.20 g of the above-mentioned Compound (1-1) and 1.11 g of triethylamine to dissolve them. 5 ml of a dichloromethane solution containing 1.15 g of methanesulfonyl chloride were dropped into the first solution therein over the course of 30 minutes at −10° C. and the solution was stirred for 30 minutes. After adding dichloromethane to the reaction solution, and washing with saturated sodium bicarbonate and saturated brine, the reaction solution was dried with anhydrous sodium sulfate. The solvent was then distilled off under reduced pressure to obtain 2.53 g of target compound (1-2). Yield: 98%

NMR (CDCl$_3$) δ: 1.42(9H,s), 2.3–2.5(4H,m), 3.00(3H,s), 3.5–3.7(4H,m), 4.24(1H,s), 4.2–4.4(2H,m), 4.8–5.0(1H,m), 5.54(1H,bd), 7.1–7.3(6H,m), 7.3–7.5(4H,m)

(3) (R)-4-diphenylmethyl-1-[3-(3-methoxycarbonylpyridin-2-yl)thio-2-t-butoxycarbonylamino]propionylpiperazine 50 ml of dimethylformamide was added to 2.53 g of the above-mentioned compound (1-2), 1.24 g of methyl 2-mercaptonicotinate and 1.01 g of potassium carbonate followed by stirring for 15 hours at room temperature. Water was added to the reaction solution followed by extraction with ethyl acetate (70 ml×3). After washing with water and saturated brine, the reaction solution was dried with anhydrous sodium sulfate. The solvent was distilled off under reduced pressure to obtain 2.89 g of residue. This residue was then purified with silica gel column chromatography (elution solvent: hexane/ethyl acetate=1/1) to obtain 2.60 g of target compound (1-3). Yield: 90%

NMR (CDCl$_3$) δ: 1.36(9H,s), 2.2–2.6(4H,m), 3.0–3.2(1H, m), 3.5–3.9(5H,m), 3.90(3H,s), 4.23(1H,s), 4.9–5.1(1H,m), 5.47(1H,bd), 7.04(1H,dd,J=7.8 Hz, 4.9 Hz), 7.1–7.3(6H,m), 7.4–7.5(4H,m), 8.16(1H,dd,J=7.8 Hz, 1.8 Hz), 8.40(1H,dd, J=4.9 Hz, 1.8 Hz)

(4) (R)-1-[2-amino-3-(3-methoxycarbonylpyridin-2-yl)thio]propionyl-4-diphenylmethylpiperazine 15 ml of 4N hydrogen chloride (ethyl acetate solution) was added to 2.36 g of the above-mentioned compound (1-3) followed by stirring for 1.5 hours at room temperature. The reaction solution was made alkaline by the addition of saturated sodium bicarbonate. After extracting with ethyl acetate (50 ml×3), the reaction solution was washed with saturated brine and dried with anhydrous sodium sulfate. The solvent was distilled off under reduced pressure to obtain 1.92 g of the target compound (1-4). Yield: 98%

NMR (CDCl$_3$) δ: 1.92(2H,bs), 2.2–2.6(4H,m), 2.84(1H, dd,J=13.9 Hz, 9.5 Hz), 3.5–3.9(5H,m), 3.93(3H,s), 4.0–4.1(1H,m), 4.24(1H,s), 7.04(1H,dd,J=7.8 Hz, 4.9 Hz), 7.1–7.3(6H,m), 7.4–7.5(4H,m), 8.19(1H,dd,J=7.8 Hz, 1.8 Hz), 8.34(1H,dd,J=4.9 Hz, 1.8 Hz)

(5) (R)-4-diphenylmethyl-1-[2-(indole-2-yl)carbonylamino-3-(3-methoxycarbonylpyridin-2-yl)thio]propionylpiperazine 15 ml of dichloromethane was added to 735 mg of the above-mentioned compound (1-4), 266 mg of indole-2-carboxylic acid and 252 mg of 1-hydroxybenzotriazole hydrate followed by the addition of 316 mg of 1-ethyl-3-(3-dimethylaminopropyl)carbodiimide hydrochloride followed by stirring for 16 hours at room temperature. After washing the reaction solution with water, saturated sodium bicarbonate and saturated brine, it was dried with anhydrous sodium sulfate. The solvent was distilled off under reduced pressure to obtain a residue. The residue was then purified with silica gel column chromatography (elution solvent: hexane/ethyl acetate=1/1) to obtain 836 mg of target compound (1-5). Yield: 88%

IR (KBr) cm$^{-1}$: 1720, 1630, 1550, 1400

NMR (CDCl$_3$) δ: 2.38(4H,bs), 3.49(1H,dd,J=13.9 Hz, 9.5 Hz), 3.5–3.9(5H,m), 3.81(3H,s), 4.19(1H,s), 5.5–5.7(1H,m), 6.9–7.4(15H,m), 7.54(1H,d,J=7.6 Hz), 7.92(1H,d,J=7.6 Hz), 8.13(1H,dd,J=7.6 Hz, 1.8 Hz), 8.42(1H,dd,J=5.6 Hz, 1.8 Hz), 9.96(1H,s)

Optical Rotation: [α]$_D^{25}$=−70.0° (c=0.9, DMSO)

(6) (R)-1-[3-(3-carboxypyridin-2-yl)thio-2-(indol-2-yl)carbonylamino]propionyl-4-diphenylmethylpiperazine 697 mg of the above-mentioned compound (1-5) was added to 8 ml of tetrahydrofuran followed by the sequential addition of 139 mg of lithium hydroxide hydrate, 8 ml of water and 4 ml of methanol and by stirring for 2 hours at room temperature. After concentrating the reaction solution to roughly 10 ml, it was neutralized with 10% citric acid and extracted with dichloromethane (30 ml×3). After washing with saturated brine, the reaction solution was dried with anhydrous sodium sulfate and the solvent was distilled off under reduced pressure to obtain 613 mg of target compound (1-6). Yield: 90%

IR (KBr) cm$^{-1}$: 1700, 1630, 1550, 1390

NMR (CDCl$_3$) δ: 2.47(2H,bs), 2.59(2H,bs), 2.88(1H,bt), 3.5–4.0(4H,m), 4.1–4.3(1H,m), 4.29(1H,s), 5.5–5.7(1H,m), 6.9–7.6(16H,m), 7.68(1H,d,J=8.9 Hz), 8.10(1H,dd,J=7.7 Hz, 1.8 Hz), 8.42(1H,dd,J=4.9 Hz, 1.8 Hz), 11.00(1H,s)

Optical Rotation: [α]$_D^{25}$=−66.9° (c=1.2, DMSO)

(7) Hydrochloride of Compound (1-6)

1.24 g of the above-mentioned compound (1-6) was dissolved in 20 ml of dichloromethane followed by the addition of 0.5 ml of 4N hydrogen chloride (ethyl acetate solution) and stirring for 10 minutes at room temperature. The solvent was distilled off under reduced pressure to obtain 1.31 g of the hydrochloride of target compound (1–6).

Melting Point: 216°–224° C.

Optical Rotation: [α]$_D^{25}$=−68.1° (c=1.1, DMSO)

IR (KBr) cm$^{-1}$: 1680, 1620, 1550, 1230

Example 2

(1) (S)-4-diphenylmethyl-1-(3-hydroxy-2-t-butoxycarbonylamino)propionylpiperidine 781 mg of target compound (2-1) was obtained by following the same procedure as (1) of Example 1 and using 673 mg of N-t-butoxycarbonyl-O-tetrahydropyranyl-L-serine and 4-diphenylmethylpiperidine instead of 1-benzhydrylpiperazine. Yield: 54%

NMR (CDCl$_3$) δ: 1.0–1.2(2H,m), 1.43(9H,s), 1.5–1.7(2H, m), 2.2–2.4(1H,m), 2.56(1H,bt), 2.8–3.1(2H,m), 3.44(1H, bd), 3.6–3.8(2H,m), 3.9–4.1(1H,m), 4.4–4.7(2H,m), 5.70(1H,bd), 7.0–7.3(10H,m)

(2) (S)-4-diphenylmethyl-1-(3-mesyloxy-2-t-butoxycarbonylamino)propionylpiperidine 916 mg of target compound (2-2) was obtained by following the same procedure as (2) of Example 1 and using 778 mg of the above-mentioned compound (2-1). Yield: 100%.

NMR (CDCl$_3$) δ: 1.0–1.3(2H,m), 1.43(9H,s), 1.6–1.7(2H, m), 2.2–2.5(1H,m), 2.60(1H,bt), 2.9–3.1(1H,m), 3.00(3H,s), 3.47(1H,dd,J=8.6 Hz, 7.1 Hz), 3.8–4.0(1H,m), 4.1–4.4(2H, m), 4.49(1H,bd), 4.8–5.0(1H,m), 5.49(1H,bd), 6.9–7.3(10H,m)

(3) (R)-4-diphenylmethyl-1-[3-(3-ethoxycarbonylpyridin-2-yl)thio-2-t-butoxycarbonylamino]propionylpiperidine 887 mg of target compound (2-3) was obtained by following the same procedure as (3) of Example 1 and using 916 mg of the above-mentioned compound (2-2) and ethyl 2-mercaptonicotinate instead of methyl 2-mercaptonicotinate. Yield: 83%

NMR (CDCl$_3$) δ: 1.0–1.3(2H,m), 1.3–1.5(12H,m), 1.5–1.7(2H,m), 2.2–2.5(1H,m), 2.55(1H,bt), 2.9–3.2(2H, m), 3.4–3.7(2H,m), 4.2–4.6(4H,m), 4.9–5.1(1H,m), 5.43 and 5.47 (total 1H,bd respectively), 6.97 and 6.99 (total 1H, dd respectively,J=7.9 Hz, 5.0 Hz, J=7.9 Hz, 5.0 Hz), 7.1–7.3 (10H,m), 8.14 and 8.16 (total 1H, dd respectively, J=7.9 Hz, 1.7 Hz, J=7.9 Hz, 1.7 Hz), 8.31 and 8.37 (total 1H, dd respectively, J=5.0 Hz, 1.7 Hz, J=5.0 Hz, 1.7 Hz)

(4) (R)-1-[2-amino-3-(3-ethoxycarbonylpyridin-2-yl)thio]propionyl-4-diphenylmethylpiperidine 738 mg of target compound (2-4) was obtained by following the same procedure as (4) of Example 1 and using 887 mg of the above-mentioned compound (2-3). Yield: 100%

NMR (CDCl₃) δ: 1.0–1.3(2H,m), 1.41 and 1.43 (total 3H, t respectively, J=7.1 Hz, J=7.1 Hz), 1.5–1.7(2H,m), 1.77(2H, bs), 2.3–2.5(1H,m), 2.5–2.7(1H,m), 2.83(1H,dd,J=13.6 Hz, 9.3 Hz), 2.9–3.1(1H,m), 3.47(1H,d,J=10.7 Hz), 3.64(1H, ddd,J=13.6 Hz, 3.9 Hz, 3.9 Hz), 4.0–4.1(1H,m), 4.2–4.5(3H, m), 4.5–4.7(1H,m), 6.97 and 6.99 (total 1H, dd respectively, J=7.9 Hz, 4.6 Hz, J=7.9 Hz, 4.6 Hz), 7.1–7.3(10H,m), 8.17(1H,bd), 8.26 and 8.34 (total 1H, dd respectively, J=4.6 Hz, 1.4 Hz, J=4.6 Hz, 1.4 Hz)

(5) (R)-4-diphenylmethyl-1-[3-(3-ethoxycarbonylpyridin-2-yl)thio-2-(indol-2-yl)carbonylamino]propionylpiperidine 865 mg of target compound (2-5) was obtained by following the same procedure as (5) of Example 1 and using 738 mg of the above-mentioned compound (2-4). Yield: 91%

NMR (CDCl₃+CD₃OD) δ: 1.0–1.3(2H,m), 1.35 and 1.37 (total 3H, t respectively, J=7.2 Hz, J=7.2 Hz), 1.5–1.8(2H, m), 2.2–2.5(1H,m), 2.62(1H,bt), 3.11(1H,bt), 3.3–3.5(2H, m), 3.65(1H,ddd,J=13.4 Hz, 12.5 Hz, 5.0 Hz), 4.2–4.6(2H, m), 4.33 and 4.37 (total 2H, q respectively, J=7.2 Hz, J=7.2 Hz), 5.5–5.7(1H,m), 6.92(1H,s), 7.03 and 7.04 (total 1H, dd respectively, J=7.8 Hz, 5.0 Hz, J=7.8 Hz, 5.0 Hz), 7.1–7.4 (12H,m), 7.58(1H,d,J=7.2 Hz), 7.64(1H,d,J=7.2 Hz), 8.17 and 8.21 (total 1H, dd respectively, J=7.8 Hz, 1.8 Hz, J=7.8 Hz, 1.8 Hz), 8.42 and 8.48 (total 1H, dd respectively, J=5.0 Hz, 1.8 Hz, J=5.0 Hz, 1.8 Hz), 9.59(1H,bs)

(6) (R)-4-diphenylmethyl-1-[3-(3-carboxypyridin-2-yl)thio-2-(indol-2-yl)carbonylamino)propionylpiperidine 307 mg of target compound (2-6) was obtained by following the same procedure as (6) of Example 1 and using 323 mg of the above-mentioned compound (2-5). Yield: 99%

IR (KBr) cm$^{-1}$: 3430, 1700, 1620, 1580, 1560

NMR (CDCl₃) δ: 1.0–1.4(2H,m), 1.6–1.8(2H,m), 2.3–2.6 (1H,m), 2.6–2.8(1H,m), 2.88(1H,bt), 3.0–3.4(1H,m), 3.51 (1H,dd,J=12.6 Hz, 12.6 Hz), 3.96(1H,bd), 4.5–4.8(2H,m), 5.5–5.6(1H,m), 6.9–7.4(14H,m), 7.38(1H,d,J=7.2 Hz), 7.52 (1H,d,J=7.2 Hz), 7.67(1H,dd,J=7.2 Hz, 7.2 Hz), 8.06(1H, bd), 8.4–8.5(1H,m), 11.01(1H,bs)

Optical Rotation: $[\alpha]_D^{25}$=−57.9° (c=1.2, DMSO)

Example 3

(1) (R)-1-[2-(5-chloroindol-2-yl)carbonylamino-3-ethoxycarbonylpyridin-2-yl)thio]propionyl-4-diphenylmethylpiperazine 1.76 g of target compound (3-1) was obtained by following the same procedures as (4) and (5) of Example 1 and using 2.00 g of (R)-1-[3-(3-ethoxycarbonylpyridin-2-yl)thio-2-(t-butoxycarbonylamino)]propionyl-4-diphenylmethylpiperazine, and 5-chloroindole-2-carboxylic acid instead of indole-2-carboxylic acid. Yield: 78%

NMR (CDCl₃) δ: 1.35(3H, t,J=7.2 Hz), 2.43(4H,bs), 3.3–3.5(1H,m), 3.6–4.0(5H,m), 4.22(1H,s), 4.30(2H,q,J=7.2 Hz), 5.5–5.7(1H,m), 6.78(1H,s), 6.9–7.5(14H,m), 7.99(1H, d,J=7.8 Hz), 8.20(1H,dd,J=7.4 Hz, 1.8 Hz), 8.45(1H,dd,J= 5.4 Hz, 1.8 Hz), 9.89(1H,s)

(2) (R)-1-[3-(3-carboxypyridin-2-yl)thio-2-(5-chloroindol-2-yl)carbonylamino]propionyl-4-diphenylmethylpiperazine 1.23 g of target compound (3-2) was obtained by following the same procedure as (6) of Example 1 and using 1.50 g of the above-mentioned compound (3-1) as a starting material. Yield: 86%

IR (KBr) cm$^{-1}$: 1710, 1630, 1550, 1450

NMR (DMSO-d₆) δ: 2.30(4H,bs), 3.1–4.0(6H,m), 4.30 (1H,s), 5.1–5.4(1H,m), 7.1–7.6(14H,m), 7.78(1H,bs), 8.12 (1H,bd), 8.55(1H,bd), 9.00(1H,d,J=8.2 Hz), 11.80(1H,s)

Optical Rotation: $[\alpha]_D^{25}$=−66.5° (c=1.0, DMSO)

Example 4

(R)-4-diphenylmethyl-1-[2-(indol-2-yl)carbonylamino-3-(3-methoxycarbonylmethyloxycarbonylpyridin-2-yl)thio]propionylpiperazine 4.78 g of the target compound was obtained by following the same procedure as (3) of Example 1 and using 5.00 g of (R)-4-diphenylmethyl-1-[3-(3-carboxypyridin-2-yl)thio-2-(indol-2-yl)carbonylamino]propionylpiperazine (compound (1-6) of Example 1) and 1.50 g of methyl bromoacetate as a starting materials. Yield: 86%

IR (KBr) cm$^{-1}$: 1760, 1720, 1630, 1550

NMR (CDCl₃) δ: 2.2–2.5(4H,m), 3.3–4.0(6H,m), 3.60 and 3.79 (total 3H, s respectively), 4.20 and 4.27 (total 1H, s respectively), 4.77, 4.84, 4.94 and 5.10 (total 2H, d respectively, J=8.3 Hz, J=8.3 Hz, 14.8 Hz, 14.8 Hz), 5.3–5.7 (1H,m), 6.8–7.5(15H,m), 7.54 and 7.60 (total 1H, d respectively, J=7.8 Hz, 7.8 Hz), 7.86 and 7.90 (total 1H, d respectively, J=8.8 Hz, 8.8 Hz), 8.2–8.3(1H,m), 8.4–8.5(1H, m), 10.00(1H,bs)

Optical Rotation: $[\alpha]_D^{25}$=−56.7° (c=1.2, DMSO)

Example 5

(R)-1-[3-(3-carboxypyridin-2-yl)thio]-2-(1-methoxycarbonylethylindol-2-yl)carbonylamino]propionyl-4-diphenylmethylpiperazine 1.10 g of the target compound was obtained by following the same procedure as (3) of Example 1 and using 5.00 g of (R)-4-diphenylmethyl-1-[3-(3-carboxypyridin-2-yl)thio-2-(indol-2-yl)carbonylamino]propionylpiperazine (compound (1-6) of Example 1) and 0.90 g of methyl acrylate. Yield: 19%

IR (KBr) cm$^{-1}$: 1730, 1640, 1540, 1450

NMR (DMSO-d₆) δ: 2.2–2.5(4H,m), 2.6–2.8(2H,m), 3.2–3.4(1H,m), 3.4–4.0(5H,m), 3.48(3H,s), 4.34(1H,s), 4.6–4.8(2H,m), 5.1–5.3(1H,m), 7.1–7.5(14H,m), 7.54(1H,d, J=8.8 Hz), 7.66(1H,d,J=7.0 Hz), 8.1–8.3(1H,m), 8.4–8.6 (1H,m), 8.85(1H,d,J=7.9 Hz)

Optical Rotation: $[\alpha]_D^{25}$=−58.2° (c=0.9, DMSO)

Example 6

(1) (R)-4-diphenylmethyl-1-[3-(3-ethoxycarbonylpyridin-2-yl)thio-2-(5-methoxyindol-2-yl)carbonylamino]propionylpiperazine 2.40 g of target compound (6-1) was obtained by following the same procedures as (4) and (5) of Example 1 and using 2.50 g of (R)-4-diphenylmethyl-1-[3-(3-ethoxycarbonylpyridin-2-yl)thio-2-t-butoxycarbonylamino]propionylpiperazine, and 5-methoxyindole-2-carboxylic acid instead of indole-2-carboxylic acid. Yield: 86%

NMR (CDCl₃) δ: 1.35(3H,t,J=7.3 Hz), 2.40(4H,bs), 3.3–3.5(1H,m), 3.6–4.0(5H,m), 3.81(3H,s), 4.21(1H,s), 4.32 (2H,q,J=7.3 Hz), 5.5–5.7(1H,m), 6.7–6.9(2H,m), 6.9–7.1 (2H,m), 7.1–7.5(11H,m), 7.65(1H,d,J=7.8 Hz), 8.18(1H,dd, J=8.0 Hz, 1.8 Hz), 8.49(1H,dd,J=5.6 Hz, 1.8 Hz), 9.54(1H, bs)

(2) (R)-1-[3-(3-carboxypyridin-2-yl)thio-2-(5-methoxyindol-2-yl)carbonylamino]propionyl-4-diphenylmethylpiperazine 1.62 g of target compound (6-2) was obtained by following the same procedure as (6) of Example 1 and using 2.00 g of the above-mentioned compound (6-1) as a starting material. Yield: 85%

IR (KBr) cm$^{-1}$: 1700, 1630, 1540, 1230

NMR (DMSO-d$_6$) δ: 2.2–2.4(4H,m), 3.2–3.8(6H,m), 3.77 (3H,s), 4.28(1H,s), 5.1–5.3(1H,m), 6.85(1H,dd,J=8.8 Hz, 2.2 Hz), 7.1–7.5(14H,m), 8.21(1H,dd,J=8.8 Hz, 1.8 Hz), 8.54(1H,dd,J=5.2 Hz, 1.8 Hz), 8.79(1H,d,J=8.5 Hz), 1.39 (1H,s)

Optical Rotation: [α]$_D^{25}$=−57.2° (c=1.1, DMSO)

Example 7

(1) (S)-4-bis(4-methoxyphenyl)methyl-1-(3-hydroxy-2-t-butoxycarbonylamino)propionylpiperazine 649 mg of target compound (7-1) was obtained, by following the same procedure as (1) of Example 1, from 578 mg of N-t-butoxycarbonyl-O-tetrahydropyranyl-L-serine using 1-bis(4-methoxyphenyl)methylpiperazine instead of 1-benzhydrylpiperazine. Yield: 65%

NMR (CDCl$_3$) δ: 1.41(9H,s), 2.36(4H,bs), 3.58(4H,bs), 3.72(1H,bs), 3.74(6H,s), 4.15(1H,s), 4.5–4.7(1H,m), 5.75 (1H,bd), 6.81(4H,d,J=8.5 Hz), 7.27(4H,d,J=8.5 Hz)

(2) (R)-4-bis(4-methoxyphenyl)methyl-1-[3-(3-ethoxycarbonylpyridin-2-yl)thio-2-t-butoxycarbonylamino]propionylpiperazine 779 mg of target compound (7-2) was obtained, by following the same procedures as (2) and (3) of Example 1, from 649 mg of the above-mentioned compound (7-1) using ethyl 2-mercaptonicotinate instead of methyl 2-mercaptonicotinate. Yield: 90%

NMR (CDCl$_3$) δ: 1.36(9H,s), 1.39(3H,t,J=7.1 Hz), 2.2–2.5(4H,m), 3.0–3.2(1H,m), 3.5–3.9(5H,m), 3.75(6H,s), 4.16(1H,s), 4.38(2H,q,J=7.1 Hz), 4.9–5.1(1H,m), 5.49(1H, bd), 6.82(4H,d,J=8.5 Hz), 7.03(1H,dd,J=7.8 Hz, 4.6 Hz), 7.29(4H,d,J=8.5 Hz), 8.20(1H,dd,J=7.8 Hz, 1.8 Hz), 8.40 (1H,dd,J=4.6 Hz, 1.8 Hz)

(3) (R)-4-bis(4-methoxyphenyl)methyl-1-[3-(3-ethoxycarbonylpyridin-2-yl)thio-2-(indol-2-yl)carbonylamino]propionylpiperazine 738 mg of target compound (7-3) was obtained by following the same procedures as (4) and (5) of Example 1 and using 779 mg of the above-mentioned compound (7-2). Yield: 89%

NMR (CDCl$_3$) δ: 1.34(3H, t,J=7.2 Hz), 2.2–2.5(4H,m), 3.3–3.5(1H,m), 3.6–3.9(5H,m), 3.75(6H,s), 4.14(1H,s), 4.32 (2H,q,J=7.2 Hz), 5.5–5.7(1H,m), 6.81(4H,d,J=8.5 Hz), 6.88 (1H,s), 7.0–7.3(4H,m), 7.27(4H,d,J=8.5 Hz), 7.57(1H,d,J= 7.6 Hz), 7.71(1H,bd), 8.18(1H,dd,J=7.8 Hz, 1.8 Hz), 8.46 (1H,dd,J=4.6 Hz, 1.8 Hz), 9.32(1H,bs)

(4) (R)-4-bis(4-methoxyphenyl)methyl-1-[3-(3-carboxypyridin-2-yl)thio-2-(indol-2-yl)carbonylamino]propionylpiperazine 670 mg of target compound (7-4) was obtained by following the same procedure as (6) of Example 1 and using 700 mg of the above-mentioned compound (7-3). Yield: 97%

IR (KBr) cm$^{-1}$: 1700, 1630, 1550, 1510

NMR (DMSO-d$_6$) δ: 2.28(4H,bs), 3.2–3.4(1H,m), 3.5–3.9(5H,m), 3.71(6H,s), 4.19(1H,s), 5.1–5.3(1H,m), 6.7–6.9(5H,m), 7.04(1H,dd,J=7.6 Hz, 7.6 Hz), 7.1–7.3(6H, m), 7.42(1H,d,J=7.6 Hz), 7.64(1H,d,J=7.6 Hz), 8.22(1H,dd, J=7.8 Hz, 1.8 Hz), 8.54(1H,dd,J=4.6 Hz, 1.8 Hz), 8.82(1H, d,J=7.7 Hz), 11.54(1H,bs)

Optical Rotation: [α]$_D^{25}$=−39.8° (c=1.3, DMSO)

Example 8

(1) (S)-4-bis(2-pyridyl)methyl-1-(3-hydroxy-2-t-butoxycarbonylamino)propionylpiperazine 343 mg of target compound (8-1) was obtained, by following the same procedure as (1) of Example 1, from 407 mg of N-t-butoxycarbonyl-O-tetrahydropyranyl-L-serine and using 1-bis(2-pyridyl)methylpiperidine instead of 1-benzhydrylpiperazine. Yield: 55%

NMR (CDCl$_3$) δ: 1.40(9H,s), 2.04(4H,bs), 3.5–3.8(7H, m), 4.5–4.7(1H,m), 4.66(1H,s), 5.76(1H,bd), 7.1–7.2(2H, m), 7.5–7.7(4H,m), 8.55(2H,d,J=4.9 Hz)

(2) (S)-4-bis(2-pyridyl)methyl-1-(3-mesyloxy-2-t-butoxycarbonylamino)propionylpiperazine 381 mg of target compound (8-2) was obtained, by following the same procedure as (2) of Example 1, from 343 mg of the above-mentioned compound (8-1). Yield: 94%

NMR (CDCl$_3$) δ: 1.42(9H,s), 2.4–2.6(4H,m), 3.03(3H,s), 3.6–3.8(4H,m), 4.2–4.4(2H,m), 4.68(1H,s), 4.8–5.0(1H,m), 5.54(1H,bd), 7.1–7.2(2H,m), 7.5–7.7(4H,m), 8.5–8.6(2H,m)

(3) (R)-4-bis(2-pyridyl)methyl-1-[3-(3-ethoxycarbonylpyridin-2-yl)thio-2-t-butoxycarbonylamino] propionylpiperazine 437 mg of target compound (8-3) was obtained, by following the same procedure as (3) of Example 1, from 381 mg of the above-mentioned compound (8-2) and using sodium hydride instead of potassium carbonate. Yield: 98%

NMR (CDCl$_3$) δ: 1.36(9H,s), 1.40(3H,t,J=7.2 Hz), 2.3–2.6(4H,m), 3.0–3.2(1H,m), 3.5–4.0(5H,m), 4.38(2H,q, J=7.2 Hz), 4.67(1H,s), 4.9–5.1(1H,m), 5.48(1H,bd), 7.05 (1H,dd,J=7.8 Hz, 4.6 Hz), 7.2–7.3(1H,m), 7.5–7.7(4H,m), 8.20(1H,dd,J=7.8 Hz, 1.8 Hz), 8.40(1H,dd,J=4.6 Hz, 1.8 Hz), 8.54(2H,d,J=4.9 Hz)

(4) (R)-4-bis(2-pyridyl)methyl-1-[3-(3-ethoxycarbonylpyridin-2 -yl)thio-2-(indol-2-yl)carbonylamino]propionylpiperazine 413 mg of target compound (8-4) was obtained, by following the same procedures as (4) and (5) of Example 1 from 437 mg of the above-mentioned compound (8-3) and using indole-2-carboxylic acid and trifluoroacetic acid instead of 4N hydrogen chloride (ethyl acetate solution). Yield: 88%

NMR (CDCl$_3$) δ: 1.34(3H,t,J=7.2 Hz), 2.47(4H,bs), 3.4–3.6(1H,m), 3.6–4.0(5H,m), 4.32(2H,q,J=7.2 Hz), 4.66 (1H,s), 5.5–5.7(1H,m), 6.89(1H,s), 7.0–7.2(5H,m), 7.26(1H, d,J=6.1 Hz), 7.5–7.7(5H,m), 7.84(1H,bd), 8.17(1H,dd,J=7.8 Hz, 1.8 Hz), 8.45(1H,dd,J=4.6 Hz, 1.8 Hz), 8.54(2H,d,J=4.9 Hz), 9.86(1H,bs)

(5) (R)-4-bis(2-pyridyl)methyl-1-[3-(3-carboxypyridin-2-yl)thio-2-(indol-2-yl)carbonylamino]propionylpiperazine 280 mg of target compound (8-5) was obtained, by following the same procedure as (6) of Example 1, from 374 mg of the above-mentioned compound (8-4). Yield: 78%

IR (KBr) cm$^{-1}$: 1700, 1630, 1550, 1430

NMR (DMSO-d$_6$) δ: 2.2–2.6(4H,bs), 3.1–3.9(6H,m), 4.7–4.9(1H,bs), 5.1–5.3(1H,m), 7.0–7.3(6H,m), 7.41(1H,d, J=8.2 Hz), 7.5–7.7(3H,m), 7.7–7.8(2H,m), 8.21(1H,dd,J= 7.8 Hz, 1.8 Hz), 8.4–8.5(2H,m), 8.55(1H,dd,J=4.6 Hz, 1.8 Hz), 8.85(1H,d,J=8.2 Hz), 11.54(1H,bs)

Optical Rotation: [α]$_D^{25}$=−61.1° (c=0.8, DMSO)

Example 9

(1) (R)-4-diphenylmethyl-1-[3-(2-methoxycarbonylphenyl) thio-2-t-butoxycarbonylamino]propionylpiperazine 868 mg of target compound (9-1) was obtained, by following the same procedures as (2) and (3) of Example 1, from 1.32 g of (S)-4-diphenylmethyl-1-(3-hydroxy-2-t-butoxycarbonylamino)propionylpiperazine and using methyl thiosalicylate acid instead of methyl 2-mercaptonicotinate. Yield: 49%

NMR (CDCl$_3$) δ: 1.42(9H,s), 2.1–2.4(4H,m), 3.1–3.3(2H, m), 3.3–3.5(2H,m), 3.5–3.7(2H,m), 3.92(3H,s), 4.15(1H,s), 4.7–4.9(1H,m), 5.52(1H,bd), 7.1–7.6(13H,m), 7.8–8.0(1H, m)

(2) (R)-4-diphenylmethyl-1-[2-(indol-2-yl)carbonylamino-3-(2-methoxycarbonylphenyl)thio]propionylpiperazine 247 mg of target compound (9-2) was obtained, by following the same procedures as (4) and (5) of Example 1, from 289 mg of the above-mentioned compound (9-1). Yield: 79%

NMR (CDCl$_3$) δ: 2.1–2.4(4H,m), 3.3–3.5(4H,m), 3.5–3.7 (2H,m), 3.90(3H,s), 4.13(1H,s), 5.3–5.5(1H,m), 6.98(1H,s), 7.0–7.4(15H,m), 7.5–7.7(3H,m), 7.89(1H,d,J=7.6 Hz)

(3) (R)-1-[3-(2-carboxyphenyl)thio-2-(indol-2-yl)carbonylamino]propionyl-4-diphenylmethylpiperazine 119 mg of target compound (9-3) was obtained, by following the same procedure as (6) of Example 1, from 148 mg of the above-mentioned compound (9-2). Yield: 82%

IR (KBr) cm$^{-1}$: 1690, 1630, 1540, 1450

NMR (CDCl$_3$) δ: 2.1–2.4(4H,m), 2.9–3.1(2H,m), 3.2–3.4 (4H,m), 4.15(1H,s), 5.2–5.4(1H,m), 6.9–7.4(17H,m), 7.5–7.7(2H,m), 8.6–8.8(1H,m), 11.34(1H,bs)

Optical Rotation: [α]$_D^{25}$=−37.2° (c=0.7, DMSO)

Example 10

(1) (S)-4-bis(4-fluorophenyl)methyl-1-(3-hydroxy-2-t-butoxycarbonylamino)propionylpiperazine 39 mg of target compound (10-1) was obtained by following the same procedure as (1) of Example 1 and using 1-bis(4-fluorophenyl)methylpiperazine instead of 1-diphenylmethylpiperazine as a starting material. Yield: 56%

NMR (CDCl$_3$) δ: 1.40(9H,s), 2.3–2.5(4H,m), 3.4–3.8(7H, m), 4.23(1H,s), 4.5–4.7(1H,m), 5.6–5.8(1H,bd), 6.99(4H, dd,J=8.6 Hz, 8.6 Hz), 7.2–7.4(4H,m)

(2) (R)-4-bis(4-fluorophenyl)methyl-1-[3-(3-ethoxycarbonylpyridin-2-yl)thio-2-t-butoxycarbonylamino] propionylpiperazine 177 mg of target compound (10-2) was obtained by following the same procedures as (2) and (3) of Example 1 and using 139 mg of the above-mentioned compound (10-1) as a starting material. Yield: 86%

NMR (CDCl$_3$) δ: 1.38(9H,s), 1.1–1.5(3H,m), 2.2–2.5(4H, m), 3.4–4.0(6H,m), 4.22(1H,s), 5.49(1H,bd), 6.9–7.1(5H, m), 7.2–7.4(4H,m), 8.1–8.3(1H,m), 8.3–8.5(1H,m)

(3) (R)-4-bis(4-fluorophenyl)methyl-1-[3-(3-ethoxycarbonylpyridin-2-yl)thio-2-(indol-2-yl)carbonylamino]propionylpiperazine 143 mg of target compound (10-3) was obtained by following the procedures of (4) and (5) of Example 1 and using 177 mg of the above-mentioned compound (10-2) as a starting material. Yield: 76%

NMR (CDCl$_3$) δ: 1.38(3H,t,J=9.2 Hz), 2.1–2.5(4H,m), 3.3–3.9(6H,m), 4.0–4.2(2H,m), 4.22(1H,s), 5.4–5.6(1H,m), 6.8–7.4(13H,m), 7.5–7.7(2H,m), 8.28(1H,d,J=7.1 Hz), 8.4–8.5(1H,m), 9.52(1H,bs)

(4) (R)-4-bis(4-fluorophenyl)methyl-1-[3-(3-carboxypyridin-2-yl)thio-2-(indol-2-yl)carbonylamino] propionylpiperazine 110 mg of target compound (10-4) was obtained by following the procedure of (6) of Example 1 and using 142 mg of the above-mentioned compound (10-3) as a starting material. Yield: 81%

IR (KBr) cm$^{-1}$: 1630, 1550, 1450, 1220

NMR (CDCl$_3$) δ: 2.3–2.7(4H,m), 3.5–4.1(6H,m), 4.21 (1H,s), 5.5–5.6(1H,m), 7.0–7.7(15H,m), 8.10(1H,d,J=7.2 Hz), 8.4–8.5(1H,m), 11.08(1H,bs)

Optical Rotation: [α]$_D^{25}$=−60.7° (c=1.0, DMSO)

Example 11

(1) (R)-4-diphenylmethyl-1-(3-hydroxy-2-t-butoxycarbonylamino)propionylpiperazine 343 mg of target compound (11-1) was obtained by following the same procedure as (1) of Example 1 and using 411 mg of N-t-butoxycarbonyl-O-tetrahydropyranyl-D-serine as a starting material. Yield: 55%

NMR (CDCl$_3$) δ: 1.21(9H,s), 2.3–2.4(4H,m), 3.4–3.8(7H, m), 4.21(1H,s), 4.5–4.6(1H,m), 5.55(1H,d,J=7.1 Hz), 7.1–7.5(11H,m)

(2) (S)-4-diphenylmethyl-1-[3-(3-methoxycarbonylpyridin-2-yl)thio-2-t-butoxycarbonylamino]propionylpiperazine 612 mg of target compound (11-2) was obtained by following the same procedures as (2) and (3) of Example 1 and using 500 mg of the above-mentioned compound (11-1) as a starting material. Yield: 90%

NMR (CDCl$_3$) δ: 1.34(9H,s), 2.2–2.5(4H,m), 3.0–3.2(2H, m), 3.4–3.7(4H,m), 3.88(3H,s), 4.20(1H,s), 4.8–5.0(1H,m), 5.43(1H,d,J=9.2 Hz), 6.9–7.4(11H,m), 7.1–7.2(1H,m), 7.3–7.4(1H,m), 7.5–7.6(1H,m)

(3) (S)-4-diphenylmethyl-1-[2-(indol-2-yl)carbonylamino-3-(3-methoxycarbonylpyridin-2-yl)thio] propionylpiperazine 598 mg of target compound (11-3) was obtained by following the same procedures as (4) and (5) of Example 1 and using 612 mg of the above-mentioned compound (11-2) as a starting material. Yield: 91%

NMR (CDCl$_3$) δ: 2.2–2.6(4H,m), 3.2–3.7(6H,m), 3.59 (3H,s), 4.00(1H,s), 5.3–5.6(1H,m), 6.6–7.2(16H,m), 7.30 (1H,d,J=7.9 Hz), 7.7–7.9(2H,m), 8.1–8.3(1H,m)

(4) (S)-4-diphenylmethyl-1-[3-(3-carboxypyridin-2-yl)thio-2-(indol-2-yl)carbonylamino]propionylpiperazine 294 mg of target compound (11-4) was obtained by following the same procedure as (6) of Example 1 and using 335 mg of the above-mentioned compound (11-3) as a starting material. Yield: 90%

IR (KBr) cm$^{-1}$: 1630, 1550, 1450

NMR (CD$_3$OD) δ: 2.1–2.6(4H,m), 3.2–4.0(7H,m), 4.2–4.3(1H,m), 5.4–5.6(1H,m), 6.98(1H,s), 6.9–7.1(1H,m), 7.1–7.5(13H,m), 7.58(1H,d,J=8.9 Hz), 8.25(1H,dd,J=10.0 Hz, 8.0 Hz), 7.4–7.5(1H,m)

Optical Rotation: [α]$_D^{25}$=+57.1° (c=0.8, DMSO)

Example 12

(1) (R)-4-diphenylmethyl-1-[3-(3-ethoxycarbonylpyridin-2-yl)thio-2-(5-hydroxyindo-2-yl)carbonylamino] propionylpiperazine 472 mg of target compound (12-1) was obtained by following the same procedures as (4) and (5) of Example 1 and using 516 mg of (R)-4-diphenylmethyl-1-[3-(3-ethoxycarbonylpyridine-2-yl)thio-2-t-butoxycarbonylamino]propionylpiperazin and 5-hydroxyindole-2-carboxylic acid, instead of indole-2-carboxylic acid, as starting materials. Yield: 53%

NMR (CD$_3$OD) δ: 1.32(3H,t,J=7.2 Hz), 2.0–2.5(4H,m), 3.1–4.0(7H,m), 4.18(2H,q,J=7.2 Hz), 5.32(1H,s), 5.3–5.6 (1H,m), 6.5–7.5(14H,m), 8.0–8.2(1H,m), 8.2–8.5(1H,m), 10.10(1H,bs)

(2) (R)-1-[3-(3-carboxypyridin-2-yl)thio-2-(5-hydroxyindol-2-yl)carbonylamino]propionyl-4-diphenylmethylpiperazine 267 mg of target compound (12-2) was obtained by following the same procedure as (6) of Example 1 and using 310 mg of the above-mentioned compound (12-1) as a starting material. Yield: 95%

IR (KBr) cm$^{-1}$: 1630, 1550, 1450

NMR (CD$_3$OD) δ: 2.2–2.6(4H,m), 3.4–4.0(6H,m), 5.35 (1H,s), 5.4–5.6(1H,m), 6.8–6.9(1H,m), 6.98(1H,s), 7.0–7.5 (15H,m), 8.2–8.3(1H,m), 8.3–8.5(1H,m)

Optical Rotation: $[\alpha]_D^{25}$=−64.0° (c=0.6, DMSO)

Example 13

(1) (S)-1-(3-hydroxy-2-t-butoxycarbonylamino)propionyl-4-isopropylpiperazine 434 mg of N-t-butoxycarbonyl-O-tetrahydropyranyl-L-serine, 230 mg of 1-isopropylpiperazine and 275 mg of 1-hydroxybenzotriazole were dissolved in 5 ml of dichloromethane followed by the addition of 345 mg of 1-ethyl-3-(3-dimethylaminopropyl)carbodiimide hydrochloride and stirring for 14 hours at room temperature. After washing the reaction solution with saturated sodium bicarbonate and saturated brine, the reaction solution was dried with anhydrous sodium sulfate. The solvent was then distilled off under reduced pressure to obtain 520 mg of residue. 4 ml of tetrahydrofuran and 4 ml of 1N hydrochloric acid were added to this residue followed by stirring for 1 hour. After making the reaction solution alkaline by adding saturated sodium bicarbonate and extracting with ethyl acetate (10 ml×3), the reaction solution was washed with saturated brine. After being dried with anhydrous sodium sulfate, the solvent was distilled off under reduced pressure to obtain 416 mg of residue. This residue was then purified by silica gel column chromatography (elution solvent: ethyl acetate/methanol=9/1) to obtain 251 mg of target compound (13-1). Yield: 53%

NMR (CDCl$_3$) δ: 1.04(6H,d,J=6.6 Hz), 1.44(9H,s), 2.4–2.6(4H,m), 2.72(1H,sep,J=6.6 Hz), 3.5–3.7(4H,m), 3.7–3.8(2H,m), 3.84(1H,bs), 4.6–4.8(1H,m), 5.84(1H,bd)

(2) (R)-1-[3-(3-ethoxycarbonylpyridin-2-yl)thio-2-t-butoxycarbonylamino]propionyl-4-isopropylpiperazine (i) 251 mg of the above-mentioned compound (13-1) and 178 mg of triethylamine was dissolved in 2 ml of dichloromethane, dropped into a dichloromethane solution containing 183 mg of methanesulfonyl chloride over the course of 10 minutes at −10° C. and stirred for 15 minutes. After adding dichloromethane to the reaction solution and sequentially washing with saturated sodium bicarbonate and saturated brine, the reaction solution was dried with anhydrous sodium sulfate. The solvent was then distilled off under reduced pressure to obtain 310 mg of residue.

(ii) 1 ml of dimethylformamide was added to 63 mg of sodium hydride (content: 60%) followed by the dropping in of a dimethylformamide solution (1 ml) containing 289 mg of ethyl 2-mercaptonicotinate over the course of 10 minutes at room temperature. The solution was then stirred for 30 minutes. The solution was then dropped into a dimethylformamide solution (2 ml) of the above-mentioned residue over the course of 10 minutes at room temperature followed by additionally stirring for 3 hours.

Water and ethyl acetate were added to the reaction solution followed by extraction with ethyl acetate (10 ml×3). The reaction was then sequentially washed with water and saturated brine followed by drying with anhydrous sodium sulfate. The solvent was distilled off under reduced pressure to obtain 669 mg of residue. This residue was then purified using silica gel column chromatography (elution solvent: ethyl acetate/methanol=9/1) to obtain 351 mg of target compound (13-2). Yield: 91%

NMR (CDCl$_3$) δ: 1.04(6H,d,J=6.3 Hz), 1.38(9H,s), 1.40 (3H,t,J=7.1 Hz), 2.4–2.6(4H,m), 2.71(1H,sep,J=6.3 Hz), 3.0–3.2(1H,m), 3.5–3.7(4H,m), 3.7–3.9(1H,m), 4.38(2H,q, J=7.1 Hz), 4.9–5.1(1H,m), 5.50(1H,bd), 7.09(1H,dd,J=7.8 Hz, 4.6 Hz), 8.23(1H,dd,J=7.8 Hz, 1.7 Hz), 8.52 (1H, dd, J=4.6 Hz, 1.7 Hz)

(3) (R)-1-[2-(indol-2-yl)carbonylamino-3-(3-ethoxycarbonylpyridin-2-yl)thio]propionyl-4-isopropyl piperazine 5 ml of 4N hydrogen chloride (ethyl acetate solution) was added to 351 mg of the above-mentioned compound (13-2) followed by stirring for 2 hours at room temperature. The reaction solution was made alkaline by the addition of saturated sodium bicarbonate, extracted with ethyl acetate (10 ml×3) and washed with saturated brine. After being dried with anhydrous sodium sulfate, the solvent was distilled off under reduced pressure to obtain 279 mg of residue. This residue was dissolved in 5 ml of dichloromethane followed by the sequential addition of 129 mg of indole-2-carboxylic acid, 123 mg of 1-hydroxybenzotriazole and 154 mg of 1-ethyl-3-(3-dimethylaminopropyl)carbodiimide hydrochloride and stirred for 15 hours at room temperature. After the reaction solution was washed with saturated sodium bicarbonate and saturated brine and dried with anhydrous sodium sulfate, the solvent was distilled off under reduced pressure to obtain 411 mg of residue. This residue was then purified with silica gel column chromatography (elution solvent: ethyl acetate/methanol=9/1) to obtain 354 mg of target compound (13-3). Yield: 92%

NMR (CDCl$_3$) δ: 0.99(6H,d,J=6.4 Hz), 1.35(3H,t,J=7.0 Hz), 2.50(4H,bs), 2.68(1H,sep,J=6.4 Hz), 3.4–3.6(1H,m), 3.6–3.9(5H,m), 4.34(2H,q,J=7.0 Hz), 5.6–5.8(1H,m), 6.94 (1H,s), 7.0–7.1(2H,m), 7.16(1H,dd,J=8.0 Hz, 8.0 Hz), 7.30 (1H,d,J=8.0 Hz), 7.56(1H,d,J=8.0 Hz), 7.96(1H,d,J=8.3 Hz), 8.19(1H,dd,J=7.6 Hz, 1.8 Hz), 8.54(1H,dd,J=4.6 Hz, 1.8 Hz), 10.05(1H,bs)

(4) (R)-1-[3-(3-carboxypyridin-2-yl)thio-2-(indol-2-yl) carbonylamino]propionyl-4-isopropylpiperazine 308 mg of the above-mentioned compound (13-3) was dissolved in 3 ml of tetrahydrofuran, followed by the sequential addition of 3 ml of water, 74 mg of lithium hydroxide hydrate and 2 ml of methanol, and stirred for 2 hours at room temperature. After concentrating the reaction solution to roughly 4 ml, it was neutralized with citric acid and extracted with dichloromethane (15 ml×3) After washing with saturated brine, the reaction solution was dried with anhydrous sodium sulfate and the solvent was distilled off under reduced pressure to obtain mg of target compound (13-4). Yield: 72%

IR (KBr) cm$^{-1}$: 1720, 1630, 1550, 1450

NMR (DMSO-d$_6$) δ: 1.00(6H,d,J=6.4 Hz), 2.4–2.9(5H, m), 3.1–3.3(1H,m), 3.4–3.6(1H,m), 3.6–3.8(3H,m), 3.8–4.0 (1H,m), 5.2–5.4(1H,m), 7.02(1H,dd,J=7.6 Hz, 7.6 Hz), 7.1–7.3(3H,m), 7.42(1H,d,J=8.2 Hz), 7.58(1H,d,J=7.6 Hz), 8.20(1H,dd,J=7.9 Hz, 1.8 Hz), 8.63(1H,dd,J=4.9 Hz, 1.8 Hz), 8.87(1H,d,J=8.2 Hz), 11.56(1H,bs)

Optical Rotation: $[\alpha]_D^{25}$=−103.9° (c=1.0, DMSO)

Example 14

(1) (S)-1-(3-hydroxy-2-t-butoxycarbonylamino )propionyl-4-(1-butylpentyl)piperazine 2.96 g of target compound (14-1) was obtained by following the same procedure as (1) of Example 1 and using 4.20 g of N-t-butoxycarbonyl-O-tetrahydropyranyl-L-serine and 1-(1-butylpentyl)piperazine, instead of 1-benzhydrylpiperazine, as starting materials. Yield: 51%

NMR (CDCl$_3$) δ: 0.8–1.0(6H,m), 1.1–1.4(13H,m), 1.49 (9H,s), 2.2–2.4(1H,m), 2.4–2.6(4H,m), 3.4–3.9(6H,m), 4.5–4.7(1H,m), 5.75(1H,bd)

(2) (S)-1-3-mesyloxy-2-t-butoxycarbonylamino)propionyl-4-(1-butylpentyl)piperazine 2.88 g of target compound (14-2) was obtained by following the same procedure as (2) (i) of Example 13 using 2.50 g of the above-mentioned compound (14-1) as a starting material. Yield: 96%

NMR (CDCl$_3$) δ: 0.8–1.0(6H,m), 1.1–1.4(12H,m), 1.49 (9H,s), 2.2–2.4(1H,m), 2.4–2.6(4H,m), 3.08(3H,s), 3.4–3.7 (4H,m), 4.2–4.4(2H,m), 4.8–5.0(1H,m), 5.55(1H,bd)

(3) (R)-1-[3-(3-ethoxycarbonylpyridin-2-yl)thio-2-t-butoxycarbonylamino]propionyl-4-(1-butylpentyl) piperazine 1.98 g of target compound (14-3) was obtained by following the same procedure as (2)(ii) of Example 13 and using 2.88 g of the above-mentioned compound (14-2) as a starting material. Yield: 58%

NMR (CDCl$_3$) δ: 0.8–1.0(6H,m), 1.1–1.6(15H,m), 1.40(9H,s), 2.2–2.7(5H,m), 3.0–3.2(1H,m), 3.4–3.9(5H, m), 4.40(2H,q,J=7.2 Hz), 4.9–5.1(1H,m), 5.50(1H,bd), 7.10 (1H,dd,J=7.6 Hz, 5.2 Hz), 8.22(1H,dd,J=7.6 Hz, 1.8 Hz), 8.61(1H,dd,J=5.2 Hz, 1.8 Hz)

(4) (R)-1-[3-(3-ethoxycarbonylpyridin-2-yl)thio-2-(indol-2-yl)carbonylamino]propionyl-4-(1-butylpentyl)piperazine 1.31 g of target compound (14-4) was obtained by following the same procedure as (3) of Example 13 and using 1.90 g of the above-mentioned compound (14-3) as a starting material. Yield: 65%

NMR (CDCl$_3$) δ: 0.8–1.0(6H,m), 1.1–1.5(15H,m), 2.3–2.5(1H,m), 2.5–2.7(4H,m), 3.3–3.6(1H,m), 3.6–4.0(5H, m), 4.37(2H,q,J=7.2 Hz), 5.5–5.7(1H,m), 6.90(1H,s), 7.0–7.4(4H,m), 7.5–7.8(2H,m), 8.20(1H,dd,J=7.8 Hz, 1.8 Hz), 8.58(1H,dd,J=5.6 Hz, 1.8 Hz), 9.50(1H,s)

(5) (R)-1-[3-(3-carboxypyridin-2-yl)thio-2-(indol-2-yl) carbonylamino]propionyl-4-(1-butylpentyl)piperazine 1.26 g of target compound (14-5) was obtained by following the same procedure as (4) of Example 13 and using 1.20 g of the above-mentioned compound (14-4) as a starting material. Yield: 97%

IR (KBr) cm$^{-1}$: 2960, 2930, 1710, 1630, 1550

NMR (DMSO-d$_6$) δ: 0.8–1.0(6H,m), 1.0–1.5(12H,m), 2.3–2.7(5H,m), 3.1–3.4(1H,m), 3.4–3.8(4H,m), 3.8–4.0(1H, m), 5.2–5.4(1H,m), 7.0–7.1(1H,m), 7.1–7.3(3H,m), 7.42 (1H,d,J=8.2 Hz), 7.62(1H,d,J=7.9 Hz), 8.27(1H,dd,J=7.8 Hz, 1.8 Hz), 8.67(1H,dd,J=5.4 Hz, 1.8 Hz), 8.85(1H,d,J=7.6 Hz), 11.54(1H,s)

Optical Rotation: [α]$_D^{25}$=−69.2° (c=1.0, DMSO)

Example 15

(1) (S)-4-diisopropylmethyl-1-(3-hydroxy-2-t-butoxycarbonylamino)propionylpiperazine 4.38 g of target compound (15-1) was obtained by following the same procedure as (1) of Example 13 and using 5.60 g of N-t-butoxycarbonyl-O-tetrahydropyranyl-L-serine and 1-diisopropylmethyl-piperazine, instead of 1-isopropylpiperazine, as starting materials. Yield: 61%

NMR (CDCl$_3$) δ: 0.8–1.0(12H,m), 1.50(9H,s), 1.8–2.0 (3H,m), 2.6–2.8(4H,m), 3.4–3.7(5H,m), 3.7–3.9(2H,m), 4.5–4.7(1H,m), 5.73(1H,bd)

(2) (R)-4-diisopropylmethyl-1-[3-(3-ethoxycarbonylpyridin-2-yl)thio-2-t-butoxycarbonylamino] propionylpiperazine 3.40 g of target compound (15-2) was obtained by following the same procedure as (2) of Example 13 and using 4.00 g of the above-mentioned compound (15-1) as a starting material. Yield: 59%

NMR (CDCl$_3$) δ: 0.8–1.0(12H,m), 1.40(9H,s), 1.3–1.5 (3H,m), 1.70(1H,bs), 1.8–2.0(2H,m), 2.6–2.9(4H,m), 3.0–3.3(1H,m), 3.4–3.9(5H,m), 4.40(2H,q,J=7.4 Hz), 4.9–5.1(1H,m), 5.50(1H,bd), 7.0–7.2(1H,m), 8.2–8.4(1H, m), 8.5–8.6(1H,m)

(3) (R)-4-diisopropylmethyl-1-[3-(3-ethoxycarbonylpyridin-2-yl)thio-2-(indol-2-yl) carbonylamino]propionylpiperazine 2.70 g of target compound (15-3) was obtained by following the same procedure as (3) of Example 13 and using 3.00 g of the above-mentioned compound (15-2) as a starting material. Yield: 83%

NMR (CDCl$_3$) δ: 0.8–1.0(12H,m), 1.39(3H,t,J=7.6 Hz), 1.8–2.0(3H,m), 2.6–2.8(4H,m), 3.4–3.9(6H,m), 4.36(2H,q, J=7.6 Hz), 5.5–5.7(1H,m), 6.90(1H,s), 7.0–7.4(5H,m), 7.60 (1H,d,J=7.8 Hz), 8.2–8.3(1H,m), 8.5–8.6(1H,m), 9.49(1H, bs)

(4) (R)-1-[3-(3-carboxypyridin-2-yl)thio-2-(indol-2-yl) carbonylamino]propionyl-4-diisopropylmethylpiperazine 2.19 g of target compound (15-4) was obtained by following the same procedure as (4) of Example 13 and using 2.50 g of the above-mentioned compound (15-3) as a starting material. Yield: 92%

IR (KBr) cm$^{-1}$: 2960, 1700, 1630, 1550

NMR (CD$_3$OD+CDCl$_3$) δ: 0.8–2.0(12H,m), 1.8–2.0(3H, m), 2.7–2.9(4H,m), 3.4–3.6(1H,m), 3.6–4.0(5H,m), 5.5–5.7 (1H,m), 7.0–7.4(4H,m), 7.41(1H,d,J=8.0 Hz), 7.60(1H,d,J= 8.0 Hz), 8.29(1H,dd,J=7.8 Hz, 1.8 Hz), 8.60(1H,dd,J=5.6 Hz, 1.8 Hz)

Optical Rotation: [α]$_D^{25}$=−73.4° (c=0.9, DMSO)

Example 16

(1) (S)-4-dicyclohexylmethyl-1-(3-hydroxy-2-t-butoxycarbonylamino)propionylpiperazine 6.43 g of target compound (16-1) was obtained by following the same procedure as (1) of Example 13 and using 7.00 g of N-t-butoxycarbonyl-O-tetrahydropyranyl-L-serine and 1-dicyclohexylmethylpiperazine instead of 1-isopropylpiperazine. Yield: 58%

NMR (CDCl$_3$) δ: 0.9–1.3(11H,m), 1.49(9H,s), 1.5–1.8 (11H,m), 1.9–2.0(1H,m), 2.6–2.8(4H,m), 3.3–3.9(7H,m), 4.5–4.7(1H,m), 5.72(1H,bd)

(2) (S)-4-dicyclohexylmethyl-1-(3-mesyloxy-2-t-butoxycarbonylamino)propionylpiperazine 6.31 g of target compound (16-2) was obtained by following the same procedure as (2) (i) of Example 13 and using 6.00 g of the above-mentioned compound (16-1) as a starting material. Yield: 90%

NMR (CDCl$_3$) δ: 0.9–1.4(11H,m), 1.49(9H,s), 1.5–1.9 (11H,m), 1.9–2.1(1H,m), 2.6–2.8(4H,m), 3.08(3H,s), 3.4–3.7(4H,m), 4.2–4.4(2H,m), 4.9–5.0(1H,m), 5.52(1H,bd)

(3) (R)-4-dicyclohexylmethyl-1-[3-(3-ethoxycarbonylpyridin-2-yl)thio-2-t-butoxycarbonylamino] propionylpiperazine 4.39 g of target compound (16-3) was obtained by following the same procedure as (2) (ii) of Example 13 and using 6.31 g of the above-mentioned compound (16-2) as a starting material. Yield: 60%

NMR (CDCl$_3$) δ: 1.40 (9H,s), 0.9–1.9(25H,m), 1.9–2.1 (1H,m), 2.6–2.8(4H,m), 3.0–3.3(1H,m), 3.4–3.9(5H,m), 4.3–4.5(2H,m), 4.9–5.1(1H,m), 5.50(1H,bd), 7.0–7.2(1H, m), 8.2–8.4(1H,m), 8.5–8.6(1H,m)

(4) (R)-4-dicyclohexylmethyl-1-[3-(3-ethoxycarbonylpyridin-2-yl)thio-2-(indol-2-yl) carbonylamino]propionylpiperazine 3.51 g of target compound (16-4) was obtained by following the same procedure as (3) of Example 13 and using 4.00 g of the above-mentioned compound (16-3) as a starting material. Yield: 82%

NMR (CDCl$_3$) δ: 0.9–1.3(11H,m), 1.40(3H, t,J=7.6 Hz), 1.4–1.8(11H,m), 1.8–2.0(1H,m), 2.6–2.8(4H,m), 3.4–3.9 (6H,m), 4.36(2H,q,J=7.6 Hz), 5.5–5.7(1H,m), 6.90(1H,s), 7.0–7.4(4H,m), 7.60(1H,d,J=7.8 Hz), 7.70(1H,d,J=7.8 Hz), 8.20(1H,dd,J=8.0 Hz, 1.8 Hz), 8.57(1H,dd,J=5.6 Hz, 1.8 Hz), 9.60(1H,s)

(5) (R)-1-[3-(3-carboxypyridin-2-yl)thio-2-(indol-2-yl) carbonylamino]propionyl-4-dicyclohexylmethylpiperazine 2.54 g of target compound (16-5) was obtained by following the same procedure as (4) of Example 13 and using 3.00 g of the above-mentioned compound (16-4) as a starting material. Yield: 89%

IR (KBr) cm$^{-1}$: 2920, 2850, 1700, 1630, 1550

NMR (CD$_3$OD+CDCl$_3$) δ: 0.9–1.3(11H,m), 1.5–1.8(11H, m), 2.0–2.2(1H,m), 2.7–2.9(4H,m), 3.4–4.0(6H,m), 5.5–5.7 (1H,m), 7.0–7.3(4H,m), 7.40(1H,d,J=8.2 Hz), 7.60(1H,d,J= 8.0 Hz), 8.27(1H,dd,J=8.0 Hz, 1.8 Hz), 8.59(1H,dd,J=5.4 Hz, 1.8 Hz)

Optical Rotation: [α]$_D^{25}$=−66.4° (c=0.9, DMSO)

Example 17

(1) (R)-4-diphenylmethyl-1-[3-(3-methoxycarbonylpyrazin-2-yl)thio-2-t-butoxycarbonylamino]propionylpiperazine 10 ml of dichloromethane was added to 606 mg of (S)-4-diphenylmethyl-1-(2-t-butoxycarbonylamino-3-hydroxy)propionylpiperazine followed by the addition of 188 mg of triethylamine and 1 ml of dichloromethane. 180 mg of methanesulfonyl chloride and 4 ml of dichloromethane were then added to this reaction solution at −10° C., and after stirring for 10 minutes, 20 ml of saturated sodium bicarbonate were added followed by stirring for 30 minutes at room temperature. After removing the aqueous layer, the reaction solution was sequentially washed with 10% hydrochloric acid, saturated sodium bicarbonate and saturated brine, after which the reaction solution was dried with anhydrous sodium sulfate and the solvent was distilled off under reduced pressure. The reaction solution was then dropped into 10 ml of a dimethylformamide suspension containing 100 mg of sodium hydride and 392 mg of 2-methoxycarbonyl-3-mercaptopyradine at 0° C. in the presence of argon followed by stirring for 12 hours at room temperature. The reaction solution was diluted with 30 ml of ethyl acetate, washed with water (30 ml×3) and saturated brine, and dried with anhydrous sodium sulfate. The solvent was distilled off under reduced pressure to obtain a residue. This residue was then purified using silica gel column chromatography (elution solvent: hexane/ethyl acetate=1/2) to obtain 352 mg of target compound (17-1). Yield: 59%

NMR (CDCl$_3$) δ: 1.37(9H,s), 2.2–2.5(4H,m), 3.0–3.2(2H, m), 3.4–3.8(4H,m), 4.00(3H,s), 4.8–5.0(1H,m), 5.52(1H,d, J=7.2 Hz), 7.1–7.5(10H,m), 8.34(1H,d,J=2.3 Hz), 8.42(1H, d,J=2.3 Hz)

(2) (R)-4-diphenylmethyl-1-[2-(indol-2-yl)carbonylamino-3-(3-methoxycarbonylpyradin-2-yl)thio]propionylpiperazine 2 ml of 4N hydrogen chloride (ethyl acetate solution) was added to 170 mg of the above-mentioned compound (17-1) and stirred for 20 minutes at room temperature. The reaction solution was diluted with 5 ml of ethyl acetate and the pH was adjusted to 8 with saturated sodium bicarbonate followed by drying with anhydrous sodium sulfate. The solvent was distilled off under reduced pressure followed by the addition of 10 ml of dichloromethane, 66 mg of indole-2-carboxylic acid, 66 mg of 1-ethyl-3-(3'-dimethylaminopropyl)carbodiimide hydrochloride and 47 mg of 1-hydroxybenzotriazole hydrate and stirring for 10 hours at room temperature. 20 ml of ethyl acetate was added to the reaction solution followed by sequentially washing with saturated sodium bicarbonate and saturated brine, and drying with anhydrous sodium sulfate. The solvent was distilled off under reduced pressure to obtain a residue. This residue was then purified using silica gel column chromatography (elution solvent: hexane/ethyl acetate=1/1) to obtain 99 mg of target compound (17-2). Yield: 55%

NMR (CDCl$_3$) δ: 2.2–2.5(4H,m), 3.3–3.5(2H,m), 3.5–3.9 (5H,m), 3.88(3H,s), 5.5–5.7(1H,m), 6.96(1H,s), 7.05(1H,dd, J=14.3 Hz, 14.3 Hz), 7.1–7.4(11H,m), 7.57(1H,d,J=9.2 Hz), 7.82(1H,d,J=9.2 Hz), 8.25(1H,d,J=2.2 Hz), 8.36(1H,d,J=2.2 Hz), 9.72(1H,s)

(3) (R)-1-[3-(3-carboxypyrazin-2-yl)thio-2-(indol-2-yl) carbonylamino)propionyl-4-diphenylmethylpiperazine 2 ml of methanol, 1 ml of tetrahydrofuran and 1 ml of water were added to 800 mg of the above-mentioned compound (17-2) to dissolve the compound followed by the addition of 200 mg of lithium hydroxide hydrate and stirring for 30 minutes at room temperature. The solvent of the reaction solution was distilled off under reduced pressure and then the residue was diluted with 10 ml of dichloromethane and washed with 10% citric acid. After drying with anhydrous sodium sulfate, the solvent was distilled off to obtain 730 mg of target compound (17-3). Yield: 93%

IR (KBr) cm$^{-1}$: 1630, 1550, 1450

NMR (CDCl$_3$) δ: 2.4–2.6(4H,m), 3.2–3.5(2H,m), 3.6–3.9 (4H,m), 4.21(1H,s), 5.52(1H,bs), 6.99(1H,s), 7.08(1H,d,J= 15.4 Hz), 7.1–7.7(12H,m), 7.45(1H,d,J=9.2 Hz), 7.58(1H, d,J=9.2 Hz), 8.23(1H,bs), 8.47(1H,bs), 9.68(1H,s)

Optical Rotation: [α]$_D^{25}$=−66.9° (c=0.1, DMSO)

Example 18

(1) (S)-4-(9-fluorenyl)-1-(3-hydroxy-2-t-butoxycarbonylamino)propionylpiperazine 839 mg of target compound (18-1) was obtained by following the same procedure as (1) of Example 1 and using 867 mg of N-t-butoxycarbonyl-O-tetrahydropyranyl-L-serine and 1-(9-fluorenyl)piperazine instead of 1-benzhydrylpiperazine. Yield: 64%

NMR (CDCl$_3$) δ: 1.39(9H,s), 2.5–2.7(4H,m), 3.3–3.4(1H, m), 3.5–3.8(6H,m), 4.5–4.6(1H,m), 4.86(1H,s), 5.66(1H, bd), 7.2–7.4(4H,m), 7.56(2H,d,J=7.6 Hz), 7.68(2H,d,J=7.6 Hz)

(2) (S)-4-(9-fluorenyl)-1-(3-mesyloxy-2-t-butoxycarbonylamino)propionylpiperazine 969 mg of target compound (18-2) was obtained by following the same procedure as (2) of Example 1 and using 839 mg of the above-mentioned compound (18-1). Yield: 98%

NMR (CDCl$_3$) δ: 1.41(9H,s), 2.62(4H,bs), 2.98(3H,s), 3.5–3.7(4H,m), 4.2–4.4(2H,m), 4.86(1H,s), 4.8–5.0(1H,m), 5.46(1H,bd), 7.2–7.4(4H,m), 7.59(2H,bd), 7.68(2H,d,J=7.6 Hz)

(3) (R)-1-[3-(3-ethoxycarbonylpyridin-2-yl)thio-2-t-butoxycarbonylamino]propionyl-4-(9-fluorenyl)piperazine 967 mg of target compound (18-3) was obtained by following the same procedure as (3) of Example 1 and using 940 mg of the above-mentioned compound (18-2) and ethyl 2-mercaptonicotinate instead of methyl 2-mercaptonicotinate. Yield: 88%

NMR (CDCl$_3$) δ: 1.37(9H,s), 1.39(3H,t,J=7.1 Hz), 2.65 (4H,bs), 3.0–3.2(1H,m), 3.5–3.9(5H,m), 4.38(2H,q,J=7.1 Hz), 4.86(1H,s), 4.9–5.1(1H,m), 5.45(1H,bd), 7.03(1H,dd, J=7.8 Hz, 4.6 Hz), 7.2–7.4(4H,m), 7.60(2H,d,J=7.6 Hz), 7.69(2H,d,J=7.6 Hz), 8.20(1H,dd,J=7.8 Hz, 1.8 Hz), 8.40 (1H,dd,J=4.6 Hz, 1.8 Hz)

(4) (R)-1-[3-(3-ethoxycarbonylpyridin-2-yl)thio-2-(indol-2-yl)carbonylamino]propionyl-4-(9-fluorenyl)piperazine 771 mg of target compound (18-4) was obtained by following the same procedures as (4) and (5) of Example 1 and using 960 mg of the above-mentioned compound (18-3). Yield: 75%

NMR (CDCl$_3$) δ: 1.33(3H, t,J=7.0 Hz), 2.64(4H,bs), 3.3–3.5(1H,m), 3.5–3.9(5H,m), 4.31(2H,q,J=7.0 Hz), 4.84 (1H,s), 5.5–5.7(1H,m), 6.88(1H,s), 7.0–7.4(8H,m), 7.5–7.7 (6H,m), 8.16(1H,dd,J=7.6 Hz, 1.5 Hz), 8.45(1H,dd,J=4.0 Hz, 1.5 Hz), 9.58(1H,s)

(5) (R)-1-[3-(3-carboxypyridin-2-yl)thio-2-(indol-2-yl) carbonylamino]propionyl-4-(9-fluorenyl)piperazine 710 mg of target compound (18-5) was obtained by following the same procedure as (6) of Example 1 and using 750 mg of the above-mentioned compound (18-4). Yield: 99%

IR (KBr) cm$^{-1}$: 1700, 1620, 1550, 1450

NMR (DMSO-d$_6$) δ: 2.38(2H,bs), 2.73(2H,bs), 3.0–3.9 (6H,m), 4.96(1H,s), 5.1–5.4(1H,m), 7.0–7.9(14H,m), 8.22 (1H,d,J=7.3 Hz), 8.5–8.7(1H,m), 8.7–9.0(1H,m), 11.57(1H, s)

Optical Rotation: [α]$_D^{25}$=−121.1° (c=0.9, DMSO)

Example 19

(1) (S)-4-(10,11-dihydro-5H-dibenzo[a,d]cyclohepten-5-yl)-1-(3-hydroxy-2-t-butoxycarbonylamino) propionylpiperazine 465 mg of target compound (19-1) was obtained by following the same procedure as (1) of Example 1 and using 578 mg of N-t-butoxycarbonyl-O-tetrahydropyranyl-L-serine and 1-(10,11-dihydro-5H-dibenzo[a,d]cyclohepten-5-yl)piperazine instead of 1-benzhydrylpiperazine. Yield: 50%

NMR (CDCl$_3$) δ: 1.42(9H,s), 2.30(4H,bs), 2.7–2.9(2H, m), 3.2–3.4(1H,m), 3.4–3.6(4H,m), 3.7–3.8(2H,m), 3.95 (1H,s), 3.9–4.1(2H,m), 4.5–4.7(1H,m), 5.68(1H,bd), 7.0–7.2 (8H,m)

(2) (S)-4-(10,11-dihydro-5H-dibenzo[a,d]cycloheptene-5-yl)-1-(3-mesyloxy-2-t-butoxycarbonylamino) propionylpiperazine 520 mg of target compound (19-2) was obtained by following the same procedure as (2) of Example 1 and using 450 mg of the above-mentioned compound (19-1). Yield: 99%

NMR (CDCl$_3$) δ: 1.44(9H,s), 2.2–2.4(4H,m), 2.7–2.9(2H, m), 3.00(3H,s), 3.4–3.6(4H,m), 3.94(1H,s), 3.9–4.1(2H,m), 4.2–4.4(2H,m), 4.8–5.0(1H,m), 5.49(1H,bd), 7.0–7.2 (8H, m)

(3) (R)-4-(10,11-dihydro-5H-dibenzo[a,d]cyclohepten-5-yl)-1-[3-(3-ethoxycarbonylpyridin-2-yl)thio-2-t-butoxycarbonylamino]propionylpiperazine 534 mg of target compound (19-3) was obtained by following the same procedure as (3) of Example 1 and using 500 mg of the above-mentioned compound (19-2) and ethyl 2-mercaptonicotinate instead of methyl 2-mercaptonicotinate. Yield: 92%

NMR (CDCl$_3$) δ: 1.37(9H,s), 1.39(3H,t,J=7.1 Hz), 2.2–2.4(4H,m), 2.7–2.9(2H,m), 3.0–3.2(1H,m), 3.4–3.8(5H, m), 3.94(1H,s), 3.9–4.1(2H,m), 4.38(2H,q,J=7.1 Hz), 4.9–5.1(1H,m), 5.46(1H,bd), 7.0–7.2(9H,m), 8.20(1H,dd,J= 7.8 Hz, 1.8 Hz), 8.38(1H,dd,J=4.6 Hz, 1.8 Hz)

(4) (R)-4-(10,11-dihydro-5H-dibenzo[a,d]cyclohepten-5-yl)-1-[3-(3-ethoxycarbonylpyridin-2-yl)thio-2-(indol-2-yl)carbonylamino]propionylpiperazine 419 mg of target compound (19-4) was obtained by following the same procedures as (4) and (5) of Example 1 and using 530 mg of the above-mentioned compound (19-3). Yield: 74%

NMR (CDCl$_3$) δ: 1.35(3H,t,J=7.0 Hz), 2.2–2.4(4H,m), 2.7–2.9(2H,m), 3.4–3.7(6H,m), 3.93(1H,s), 4.0–4.1(2H,m), 4.34(2H,q,J=7.0 Hz), 5.5–5.7(1H,m), 6.89(1H,s), 7.0–7.4 (12H,m), 7.58(1H,d,J=7.9 Hz), 7.70(1H,d,J=8.2 Hz), 8.19 (1H,dd,J=7.9 Hz, 1.8 Hz), 8.46(1H,dd,J=4.6 Hz, 1.8 Hz), 9.58(1H,s)

(5) (R)-1-[3-(3-carboxypyridin-2-yl)thio-2-(indol-2-yl) carbonylamino]propionyl-4-(10,11-dihydro-5H-dibenzo[a, d]cyclohepten-5-yl)piperazine 358 mg of target compound (19-5) was obtained by following the same procedure as (6) of Example 1 and using 410 mg of the above-mentioned compound (19-4). Yield: 91%

IR (KBr) cm$^{-1}$: 1700, 1630, 1550, 1450

NMR (DMSO-d$_6$) δ: 2.19(4H,bs), 2.6–2.9(2H,m), 3.1–3.8(6H,m), 3.8–4.0(2H,m), 3.95(1H,s), 5.2–5.4(1H,m), 7.0–7.3(12H,m), 7.43(1H,d,J=8.2 Hz), 7.64(1H,d,J=7.9 Hz), 8.24(1H,d,J=7.6 Hz), 8.5–8.6(1H,m), 8.8–8.9(1H,m), 11.56 (1H,s)

Optical Rotation: [α]$_D^{25}$=−52.2° (c=1.3, DMSO)

Example 20

(1) (R)-1-[2-(5-chloroindol-2-yl)carbonylamino-3-(3-ethoxycarbonylpyridin-2-yl)thio]propionyl-4-diphenylmethylpiperidine 5.01 g of target compound (20-1) was obtained by following the same procedures as (4) and (5) of Example 1 and using 6.00 g of (R)-1-[3-(3-ethoxycarbonylpyridin-2-yl) thio-2-t-butoxycarbonylamino]propionyl-4-diphenylmethylpiperidine (compound (2-3) of Example 2), and 5-chloroindole-2-carboxylic acid, instead of indole-2-carboxylic acid, as starting materials. Yield: 74%

NMR (CDCl$_3$) δ: 1.0–1.4(5H,m), 1.5–1.7(2H,m), 2.2–2.5 (1H,m), 2.65(1H,bt), 3.13(1H,bt), 3.3–3.5(2H,m), 3.6–3.8 (1H,m), 4.2–4.5(3H,m), 4.5–4.7(1H,m), 5.5–5.7(1H,m), 6.79(1H,s), 6.9–7.4(14H,m), 7.49(1H,s), 7.9–8.1(1H,m), 8.1–8.3(1H,m), 8.3–8.5(1H,m), 9.85 and 10.00 (total 1H,s respectively)

(2) (R)-1-[3-(3-carboxypyridin-2-yl)thio-2-(5-chloroindol-2-yl)carbonylamino]propionyl-4-diphenylmethylpiperidine 4.46 g of target compound (20-2) was obtained by following the same procedure as (6) of Example 1 and using 5.00 g of the above-mentioned compound (20-1) as a starting material. Yield: 93%

IR (KBr) cm$^{-1}$: 1700, 169.0, 1550, 1450

NMR (CDCl$_3$+CD$_3$OD) δ: 0.9–1.3(2H,m), 1.5–1.7(2H, m), 2.3–2.8(2H,m), 3.0–3.3(1H,m), 3.3–3.5(2H,m), 3.6–3.8 (1H,m), 4.3–4.6(2H,m), 5.4–5.7(1H,m), 7.0–7.4(14H,m), 7.46(1H,bs), 8.2–8.4(1H,m), 8.4–8.6(1H,m)

Optical Rotation: [α]$_D^{25}$=−61.5° (c=0.9, DMSO)

Example 21

(1) (R)-4-diphenylmethyl-1-[3-(3-ethoxycarbonylpyridin-2-yl)thio-2-(5-methoxyindol-2-yl)carbonylamino] propionylpiperidine 5.18 g of target compound (21-1) was obtained by following the same procedures as (4) and (5) of Example 1 and using 6.00 g of (R)-1-[3-(3-ethoxycarbonylpyridin-2-yl) thio-2-t-butoxycarbonylamino]propionyl-4-diphenylmethylpiperidine (compound (2-3) of Example 2), and 5-methoxyindole-2-carboxylic acid, instead of indole-2-carboxylic acid, as starting materials. Yield: 77%

NMR (CDCl$_3$) δ: 1.0–1.4(5H,m), 1.5–1.8(2H,m), 2.2–2.5 (1H,m), 2.5–2.7(1H,m), 2.9–3.2(1H,m), 3.3–3.5(2H,m), 3.6–3.8(1H,m), 3.81(3H,s), 4.2–4.5(3H,m), 4.5–4.7(1H,m), 5.5–5.8(1H,m), 6.83(2H,s), 6.9–7.1(2H,m), 7.1–7.4(11H, m), 7.6–7.8(1H,m), 8.1–8.3(1H,m), 8.46(1H,dd,J=12.4 Hz, 4.1 Hz), 9.64 and 9.70(total 1H, s respectively)

(2) (R)-1-[3-(3-carboxypyridin-2-yl)thio-2-(5-methoxyindol-2-yl)carbonylamino]propionyl-4-diphenylmethylpiperidine 4.51 g of target compound (21-2) was obtained by following the same procedure as (6) of Example 1 and using 5.00 g of the above-mentioned compound (21-1) as a starting material. Yield: 94%

IR (KBr) cm$^{-1}$: 1700, 1620, 1550, 1450

NMR (CDCl$_3$) δ: 1.0–1.3(2H,m), 1.5–1.9(2H,m), 2.3–2.5 (1H,m), 2.5–2.8(1H,m), 2.9–3.3(2H,m), 3.49(1H,t,J=9.9 Hz), 3.73(3H,s), 3.8–4.0(1H,m), 4.5–4.8(2H,m), 5.5–5.7 (1H,m), 6.8–7.0(3H,m), 6.88(1H,s), 7.0–7.1(1H,m), 7.1–7.4 (10H,m), 7.7–7.9(1H,m), 8.0–8.2(1H,m), 8.43(1H,dd,J= 11.0 Hz, 3.1 Hz), 10.75(1H,s)

Optical Rotation: [α]$_D^{25}$=−55.8° (c=1.2, DMSO)

Example 22

(1) (R)-1-[3-(3-diisopropoxyphosphorylpyridin-2-yl)thio-2-t-butoxycarbonylamino]propionyl-4-diphenylmethylpiperazine 3.34 g of target compound (21-1) was obtained by following the same procedures as (2) and (3) of Example 1 and using 2.20 g of (S)-4-diphenylmethyl-1-(3-hydroxy-2-t-butoxycarbonylamino)propionylpiperazine (compound (1-1) of Example 1), and diisopropyl (1,2-dihydro-2-thioxo-3-pyridyl)phosphonate instead of methyl 2-mercaptonicotinate. Yield: 96%

NMR (CDCl$_3$) δ: 1.25(3H,d,J=6.1 Hz), 1.28(3H,d,J=6.1 Hz), 1.38(9H,s), 1.39(6H,d,J=6.1 Hz), 2.3–2.5(4H,m), 3.1–3.3(1H,m), 3.5–3.9(5H,m), 4.24(1H,s), 4.6–4.8(2H,m), 4.9–5.1(1H,m), 5.51(1H,bd), 7.02(1H,ddd,J=7.3 Hz, 4.6 Hz, 2.3 Hz), 7.1–7.3(6H,m), 7.3–7.5(4H,m), 8.14(1H,ddd, J=14.1 Hz, 7.3 Hz, 2.3 Hz), 8.34(1H,ddd,J=4.6 Hz, 2.3 Hz, 2.3 Hz)

(2) (R)-1-[2-amino-3-(3-diisopropoxyphosphorylpyridin-2-yl)thio]propionyl-4-diphenylmethylpiperazine 1.11 g of target compound (22-2) was obtained by following the same procedure as (4) of Example 1 and using 1.34 g of the above-mentioned compound (22-1). Yield: 97%

NMR (CDCl$_3$) δ: 1.27(3H,d,J=6.3 Hz), 1.29(3H,d,J=6.3 Hz), 1.41(6H,d,J=6.3 Hz), 1.86(2H,bs), 2.3–2.6(4H,m), 2.89 (1H,dd,J=13.9 Hz, 9.5 Hz), 3.5–3.9(5H,m), 4.04(1H,dd,J= 9.5 Hz, 3.4 Hz), 4.24(1H,s), 4.6–4.8(2H,m), 7.04(1H,ddd, J=7.3 Hz, 4.6 Hz, 2.3 Hz), 7.1–7.3(6H,m), 7.3–7.5(4H,m), 8.14(1H,ddd,J=14.1 Hz, 7.3 Hz, 2.3 Hz), 8.30(1H,ddd,J=4.6 Hz, 2.3 Hz, 2.3 Hz)

(3) (R)-1-[3-(3-diisopropoxyphosphorylpyridin-2-yl)thio-2-(indol-2-yl)carbonylamino]propionyl-4-diphenylmethylpiperazine 1.37 g of target compound (22-3) was obtained by following the same procedure as (5) of Example 1 and using 1.11 g of the above-mentioned compound (22-2). Yield: 99%

NMR (CDCl$_3$) δ: 1.17(3H,d,J=6.2 Hz), 1.20(3H,d,J=6.2 Hz), 1.29(3H,d,J=6.2 Hz), 1.34(3H,d,J=6.2 Hz), 2.3–2.5 (4H,m), 3.4–3.9(6H,m), 4.22(1H,s), 4.6–4.8(2H,m), 5.4–5.6 (1H,m), 6.85(1H,s), 7.0–7.5(14H,m), 7.58(1H,d,J=7.9 Hz), 7.69(1H,d,J=8.2 Hz), 8.12(1H,ddd,J=14.1 Hz, 7.3 Hz, 2.3 Hz), 8.42(1H,ddd,J=4.6 Hz, 2.3 Hz, 2.3 Hz), 9.51(1H,bs)

(4) (R)-4-diphenylmethyl-1-[3-(3-phosphonopyridin-2-yl)thio-2-(indol-2-yl)carbonylamino]propionylpiperazine 458 mg of the above-mentioned compound (22-3) was dissolved in 6 ml of dimethylformamide followed by the addition of 1.16 g of bromotrimethylsilane and stirring for 18 hours at room temperature. Water was added to the reaction solution and the precipitated crystals were filtered and washed with water followed by drying under reduced pressure to obtain 334 mg of target compound (22-4). Yield: 82%

IR (KBr) cm$^{-1}$: 1640, 1540, 1460, 1380

NMR (DMSO-d$_6$) δ: 2.2–2.5(4H,m), 3.3–3.9(6H,m), 4.37 (1H,s), 5.1–5.3(1H,m), 7.0–7.5(15H,m), 7.62(1H,d,J=7.6 Hz), 7.9–8.1(1H,m), 8.3–8.4(1H,m), 8.90(1H,d,J=7.9 Hz), 11.56(1H,s)

Optical Rotation: [α]$_D^{25}$=−40.3° (c=1.2, DMSO)

Example 23

(1) (S)-1-(4-benzyloxycarbonyl-2-t-butoxycarbonylamino) butyryl-4-diphenylmethylpiperazine 2.0 g of γ-benzyl N-t-butoxycarbonyl-L-glutamate was dissolved in 30 ml of tetrahydrofuran followed by the addition of 1.8 g of 1-benzhydrylpiperazine, 1.47 g of N,N'-dicyclohexylcarbodiimide and 960 mg of 1-hydroxybenzotriazole hydrate and stirred for 3 hours at room temperature. The reaction solution was diluted with 50 ml of ethyl acetate, washed with saturated sodium bicarbonate and saturated brine, and dried with anhydrous sodium sulfate, after which the solvent was distilled off under a reduced pressure. The reaction solution was then purified with silica gel column chromatography (elution solvent: ethyl acetate/hexane=1/1) to obtain 3.3 g of target compound (23-1). Yield: 98%

NMR (CDCl$_3$) δ: 1.40(9H,s), 1.5–2.0(2H,m), 2.2–2.5(6H, m), 3.5–3.7(4H,m), 4.20(1H,s), 4.5–4.7(1H,m), 5.12(2H, bs), 5.48(1H,bd), 7.1–7.5(15H,m)

(2) (S)-4-diphenylmethyl-1-(5-hydroxy-2-t-butoxycarbonylamino)valerylpiperazine 50 ml of ethanol was added to 1.0 g of the above-mentioned compound (23-1) followed by the addition of 132 mg of sodiumborohydride and refluxing while heating for 3 hours. After distilling off the solvent under reduced pressure, the reaction solution was diluted with 50 ml of ethyl acetate, washed with 10% ammonium chloride, saturated sodium bicarbonate and saturated brine, and dried with anhydrous sodium sulfate. The solvent was distilled off under reduced pressure to obtain a residue. This residue was then purified with silica gel column chromatography (elution solvent: ethyl acetate/hexane=2/1) to obtain 586 mg of target compound (23-2). Yield: 72%

NMR (CDCl$_3$) δ: 1.42(9H,s), 1.4–1.8(4H,m), 2.3–2.5(4H, m), 3.4–3.8(6H,m), 4.20(1H,s), 4.6–4.8(1H,m), 5.53(1H,d, J=7.3 Hz), 7.1–7.6(10H,m)

(3) (S)-1-(5-azido-2-t-butoxycarbonylamino)valeryl-4-diphenylmethylpiperazine 30 ml of dichloromethane was added to 2.0 g of the above-mentioned compound (23-2) to dissolve the compound, followed by the addition of 565 mg of triethylamine. 588 mg of methanesulfonyl chloride together with 10 ml of dichloromethane was added at 0° C. and the mixture was stirred for 5 minutes. After adding 50 ml of saturated sodium bicarbonate and stirring for 30 minutes at room temperature, the aqueous layer was removed. After washing with 10% hydrochloric acid and saturated sodium bicarbonate and drying with anhydrous sodium sulfate, the solvent was distilled off under a reduced pressure followed by the addition of 15 ml of N,N'-dimethylimidazolidinone. The mixture was then added to 556 mg of sodium azide in the presence of argon followed by stirring for 10 hours at room temperature. The reaction solution was diluted with 50 ml of ethyl acetate, washed with water (30 ml×3), and dried with anhydrous sodium sulfate. The solvent was distilled off to obtain a residue. This residue was then purified using silica gel column chromatography (elution solvent: ethyl acetate/hexane=2/1) to obtain 1.6 g of target compound (23-3). Yield: 77%

NMR (CDCl₃) δ: 1.21(9H,s), 1.5–2.0(4H,m), 2.2–2.4(4H, m), 3.2–3.4(2H,m), 3.4–3.7(4H,m), 4.22(1H,s), 4.4–4.6(1H, m), 5.45(1H,bd), 7.1–7.4(10H,m)

(4) (S)-1-[5-(4,5-dimethoxycarbonyl-1,2,3-triazol-1-yl)-2-t-butoxycarbonylamino]valeryl-4-diphenylmethylpiperazine 10 ml of 1,2-dichloroethane and 120 mg of dimethyl acetylenedicarboxylate were added to 205 mg of the above-mentioned compound (23-3) and refluxed while heating for 5 hours. After distilling off the solvent under a reduced pressure, the residue was purified using silica gel column chromatography (elution solvent: ethyl acetate/hexane=1/1) to obtain 238 mg of target compound (23-4). Yield: 90%

NMR (CDCl₃) δ: 1.21(9H,s), 1.5–2.1(4H,m), 2.2–2.5(4H, m), 3.4–3.7(6H,m), 3.98(3H,s), 4.15(3H,s), 4.23(1H,s), 5.60 (1H,bd), 7.1–7.5(10H,m)

(5) (S)-1-[5-(4,5-dimethoxycarbonyl-1,2,3-triazol-1-yl)-2-(indol-2-yl)carbonylamino]valeryl-4-diphenylmethylpiperazine 3 ml of trifluoroacetic acid was added to 982 mg of the above-mentioned compound (23-4) followed by stirring for 30 minutes at room temperature. After distilling off the solvent under a reduced pressure, the reaction solution was diluted with 20 ml of ethyl acetate. The reaction solution was then washed with saturated sodium bicarbonate and dried with anhydrous sodium sulfate. The solvent was distilled off under a reduced pressure and the residue was dissolved in 20 ml of dichloromethane. 247 mg of indole-2-carboxylic acid, 248 mg of 1-ethyl-3-(3-dimethylaminopropyl)carbodiimide hydrochloride and 175 mg of 1-hydroxybenzotriazole hydrate were added followed by stirring for 10 hours at room temperature. 50 ml of ethyl acetate was added to the reaction solution followed by washing with saturated sodium bicarbonate and saturated brine, and drying with anhydrous sodium sulfate. The solvent was distilled off under a reduced pressure to obtain a residue. This was then purified using silica gel column chromatography (elution solvent: hexane/ethyl acetate=1/1) to obtain 844 mg of the target compound (23-5). Yield: 82%

NMR (CDCl₃) δ: 1.5–2.1(4H,m), 2.2–2.5(4H,m), 3.4–3.8 (4H,m), 3.96(3H,s), 4.05(3H,s), 4.24(1H,s), 4.5–4.8(2H,m), 5.1–5.3(1H,m), 7.0–7.8(16H,m), 9.55(1H,bs)

(6) (S)-1-[5-(4,5-dicarboxy-1,2,3-triazol-1-yl)-2-(indol-2-yl)carbonylamino]valeryl-4-diphenylmethylpiperazine 4 ml of tetrahydrofuran, 4 ml of methanol and 2 ml of water were added to 380 mg of the above-mentioned compound (23-5) to dissolve the compound. 180 mg of lithium hydroxide hydrate was added followed by stirring for 30 minutes at room temperature. After distilling off the solvent under reduced pressure, the reaction solution was diluted by addition of 10 ml of dichloromethane. The reaction solution was washed with 10% citric acid and dried with anhydrous sodium sulfate. The solvent was then distilled off under reduced pressure to obtain 332 mg of the target compound (23-6). Yield: 90%

IR (KBr) cm⁻¹: 1630, 1550, 1450

NMR (CD₃OD) δ: 1.6–2.1(4H,m), 2.3–2.7(4H,m), 3.2–3.8(4H,m), 4.02(1H,s), 4.92(2H,bs), 5.12(1H,bs), 7.0–7.8(16H,m), 8.1–8.3(1H,m), 11.23(1H,s)

Optical Rotation: [α]$_D^{25}$=+16.8° (c=1.2, DMSO)

Example 24

(1) (S)-1-(4-azido-2-t-butoxycarbonylamino)butyryl-4-diphenylmethylpiperazine 5.00 g of target compound (24-1) was obtained by following the same procedure as (3) of Example 23 and using 7.10 g of (S)-4-diphenylmethyl-1-(4-mesyloxy-2-t-butoxycarbonylamino)butyrylpiperazine as a starting material. Yield: 89%

NMR (CDCl₃) δ: 1.42(9H,s), 1.6–1.9(1H,m), 2.3–2.5(5H, m), 2.3–2.5(4H,m), 3.3–3.7(6H,m), 4.25(1H,s), 4.6–4.8 (1H, m), 5.50 (1H, bd), 7.1–7.5 (10H,m)

(2) (S)-4-diphenylmethyl-1-[4-(5-methoxycarbonyl-1,2,3-triazol-1-yl)-2-t-butoxycarbonylamino]butyrylpiperazine 0.84 g of target compound (24-2) was obtained by following the same procedure as (4) of Example 23 and using 5.00 g of the above-mentioned compound (24-1) and methyl propiolate, instead of dimethyl acetylenedicarboxylate, as starting materials. Yield: 14%

NMR (CDCl₃) δ: 1.40(9H,S), 2.2–2.5(6H,m), 3.4–3.7 (4H,m), 3.88(3H,s), 4.21(1H,s), 4.5–5.0(2H,m), 5.2–5.3(1H, m), 5.65(1H,bd), 7.1–7.5(10H,m), 8.10(1H,s)

(3) (S)-1-[4-(5-carboxy-1,2,3-triazol-1-yl)-2-(indol-2-yl)carbonylamino]butyryl-4-diphenylmethylpiperazine 0.39 g of target compound (24-3) was obtained by following the same procedures as (5) and (6) of Example 23 using 0.80 g of the above-mentioned compound (24-2) as a starting material. Yield: 46%

IR (KBr) cm⁻¹: 1700, 1650, 1550, 1450

NMR (CD₃OD) δ: 2.3–2.7(6H,m), 3.5–3.8(4H,m), 4.50 (1H,s), 4.8–5.1(3H,m), 7.0–7.7(15H,m), 8.10(1H,s)

Optical Rotation: [α]$_D^{25}$=−3.5° (c=0.2, DMSO)

Example 25

(1) (S)-1-(3-benzyloxycarbonyl-2-t-butoxycarbonylamino)propionyl-4-diphenylmethylpiperazine 7.40 g of target compound (25-1) was obtained by following the same procedure as (1) of Example 23 and using 3.00 g of β-benzyl N-t-butoxycarbonyl-L-aspartate as a starting material. Yield: 98%

NMR (CDCl₃) δ: 1.40(9H,s), 2.34(4H,bs), 2.5–2.9(2H, m), 3.4–3.8(4H,m), 4.21(1H,s), 4.8–5.0(1H,m), 5.09(2H,s), 5.54(1H,bd), 7.1–7.6(10H,m)

(2) (S)-1-(3-carboxy-2-t-butoxycarbonylamino)propionyl-4-diphenylmethylpiperazine 5.82 g of target compound (25-2) was obtained by following the same procedure as (6) of Example 23 and using 7.40 g of the above-mentioned compound (25-1) as a starting material. Yield: 91%

NMR (CDCl₃) δ: 1.40(9H,s), 2.39(4H,bs), 2.5–2.9(2H, m), 3.4–3.8(4H,m), 4.24(1H,s), 4.7–5.0(1H,m), 5.74(1H, bd), 7.1–7.5(10H,m), 8.00(1H,bs)

(S)-4-diphenylmethyl-1-(3-succimidoxycarbonyl-2-t-butoxycarbonylamino)propionylpiperazine 30 ml of acetonitrile was added to 5.80 g of the above-mentioned compound (25-2) followed by the addition of 1.18 g of pyridine together with 10 ml of acetonitrile. Next, 4.23 g of disuccinimidyl oxalate suspended in 20 ml of acetonitrile was added, followed by stirring for 1 hour at room temperature. The reaction solution was distilled under reduced pressure and the resulting residue was dissolved in 60 ml of ethyl acetate, washed with water (40 ml×3) and dried with anhydrous sodium sulfate. The solvent was distilled off under reduced pressure to obtain 6.96 g of residue in the form of the target compound (25-3). Yield: 99%

NMR (CDCl₃) δ: 1.40(9H,s), 2.2–2.5(4H,m), 2.80(4H,s), 2.7–3.1(2H,m), 3.4–3.8(4H,m), 4.25(1H,s), 4.9–5.1(1H,m), 5.50(1H,bd), 7.1–7.5(10H,m)

(4) (S)-4-diphenylmethyl-1-(4-hydroxy-2-t-butoxycarbonylamino)butyrylpiperazine 60 ml of tetrahydrofuran was added to 6.00 g of the above-mentioned compound (25-3) to dissolve the compound, followed by the addition of 1.00 g of sodium borohydride and stirring for 1 hour at room temperature. The reaction solution was distilled under reduced pressure and the resulting residue was dissolved in 60 ml of ethyl acetate, washed with 10% hydrochloric acid and saturated sodium bicarbonate, and dried with anhydrous sodium sulfate. The solvent was distilled off under reduced pressure to obtain 3.14 g of residue in the form of target compound (25-4). Yield: 65%

NMR (CDCl$_3$) δ: 1.2–1.6(1H,m), 1.7–2.0(1H,m), 1.43 (9H,s), 2.38(4H,bs), 3.3–3.9(7H,m), 4.24(1H,s), 4.6–4.8 (1H,m), 5.78(1H,bd), 7.1–7.5(10H,m)

(5) (S)-4-diphenylmethyl-1-[4-(3-ethoxycarbonylpyridin-2-yl)thio-2-t-butoxycarbonylamino]butyrylpiperazine 1.34 g of triethylamine and 20 ml of dichloromethane were added to 3.00 g of the above-mentioned compound (25-4) to dissolve followed by stirring while cooling to −10° C. A solution, in which 1.52 g of methanesulfonyl chloride was added to 10 ml of dichloromethane, was then dropped into the reaction solution. The reaction solution was diluted with dichloromethane 5 minutes after the completion of the dropping, sequentially washed with saturated sodium bicarbonate, 10% hydrochloric acid and saturated sodium bicarbonate, and then dried with anhydrous sodium sulfate. The solvent was distilled off under reduced pressure to obtain 3.48 g of residue.

This residue was dissolved in 35 ml of dimethylformamide followed by the addition of 1.68 g of ethyl 2-mercaptonicotinate and 1.27 g of potassium carbonate and stirring for 18 hours at room temperature. The reaction solution was diluted with ethyl acetate, washed three times with water and dried with anhydrous sodium sulfate. The solvent was distilled off under reduced pressure to obtain 3.73 g of residue. This residue was then purified with silica gel column chromatography (elution solvent: hexane/ethyl acetate=1/1) to obtain 2.90 g of target compound (25-5). Yield: 71%

NMR (CDCl$_3$) δ: 1.2–1.4(3H,m), 1.48(9H,s), 2.0–2.6(6H, m), 3.1–3.3(2H,m), 3.52 and 3.6–3.8(total 4H,bs,m), 4.19 (1H,s), 4.2–4.5(2H,m), 4.6–4.8(1H,m), 5.59(1H,bd), 6.9–7.1(1H,m), 7.1–7.5(10H,m), 8.1–8.3(1H,m), 8.4–8.5 (1H,m)

(6) (S)-4-diphenylmethyl-1-[4-(3-ethoxycarbonylpyridin-2-yl)thio-2-(indol-2-yl)carbonylamino]butyrylpiperazine 2.16 g of target compound (25-6) was obtained by following the same procedure as (5) of Example 23 and using 2.90 g of the above-mentioned compound (25-5) as a starting material. Yield: 70%

NMR (CDCl$_3$) δ: 1.36(3H, t,J=7.2 Hz), 2.0–2.5(6H,m), 3.1–3.4(2H,m), 3.4–3.8(4H,m), 4.15(1H,s), 4.31(2H,q,J=7.2 Hz), 5.2–5.5(1H,m), 6.8–7.0(1H,m), 7.0–7.5(14H,m), 7.60 (1H,d,J=7.6 Hz), 7.7–8.0(1H,m), 8.10(1H,d,J=7.6 Hz), 8.3–8.4(1H,m), 9.09(1H,bs)

(7) (S)-1-[4-(3-carboxypyridin-2-yl)thio-2-(indol-2-yl)carbonylamino]butyryl-4-diphenylmethylpiperazine 1.05 g of target compound (25-7) was obtained by following the same procedure as (6) of Example 23 and using 2.00 g of the above-mentioned compound (25-6) as a starting material. Yield: 55%

IR (KBr) cm$^{-1}$: 1700, 1630, 1550, 1450

NMR (CDCl$_3$+CD$_3$OD) δ: 2.0–2.6(6H,m), 3.1–3.4(2H, m), 3.5–3.9(4H,m), 4.20(1H,s), 5.2–5.4(1H,m), 6.9–7.6 (15H,m), 7.69(1H,d,J=7.8 Hz), 8.20(1H,dd,J=7.6 Hz, 1.8 Hz), 8.40(1H,dd,J=5.6 Hz, 1.8 Hz)

Optical Rotation: [α]$_D^{25}$=+1.0° (c=1.0, DMSO)

Example 26

(1) (S)-1-(4-benzyloxycarbonyl-2-t-butoxycarbonylamino)butyryl-4-diphenylmethylpiperazine 674 mg of γ-benzyl N-t-butoxycarbonyl-L-glutamate, 554 mg of 1-benzhydrylpiperazine and 337 mg of 1-hydroxybenzotriazole hydrate were dissolved in 13 ml of dichloromethane followed by the addition of 421 mg of 1-ethyl-3-(3-dimethylaminopropyl)carbodiimide hydrochloride and stirring for 14 hours at room temperature. After washing the reaction solution with saturated sodium bicarbonate and saturated brine, and drying with anhydrous sodium sulfate, the solvent was distilled off under reduced pressure to obtain 1.38 g of residue. This was then purified with silica gel column chromatography (elution solvent: hexane/ethyl acetate=1/1) to obtain 971 mg of target compound (26-1). Yield: 85%

NMR (CDCl$_3$) δ: 1.40(9H,s), 1.5–2.0(2H,m), 2.2–2.5(6H, m), 3.5–3.7(4H,m), 4.20(1H,s), 4.5–4.7(1H,m), 5.12(2H, bs), 5.48(1H,bd), 7.1–7.5(15H,m)

(2) (S)-1-(4-carboxy-2-t-butoxycarbonylamino)butyryl-4-diphenylmethylpiperazine 914 mg of the above-mentioned compound (26-1) was dissolved in 7 ml of tetrahydrofuran followed by the addition of 202 mg of lithium hydroxide hydrate, 7 ml of water and 4 ml of methanol and stirring for 1 hour at room temperature. After concentrating the reaction solution to roughly 10 ml, it was washed with ether (10 ml×3). After being neutralized by the addition of 10% citric acid, the reaction solution was extracted with dichloromethane (10 ml×3) and washed with saturated brine. After drying with anhydrous sodium sulfate, the solvent was distilled off under reduced pressure to obtain 708 mg of target compound (26-2). Yield: 92%

NMR (CDCl$_3$) δ: 1.40(9H,s), 1.5–2.0(2H,m), 2.2–2.5(6H, m), 3.5–3.7(4H,m), 4.23(1H,s), 4.5–4.7(1H,m), 5.66(1H, bd), 7.2–7.4(6H,m), 7.4–7.5(4H,m)

(3) (S)-4-diphenylmethyl-1-[4-(4-methoxycarbonyloxazol-5-yl)-2-t-butoxycarbonylamino]butyrylpiperazine 385 mg of the above-mentioned compound (26-2) was dissolved in 7 ml of dimethylformamide followed by the sequential addition of 330 mg of diphenylphosphorylazide, 221 mg of potassium carbonate and 317 mg of methyl isocyanoacetate and stirred for 19 hours at room temperature. After adding ethyl acetate and saturated brine to the reaction solution and extracting with ethyl acetate (10 ml×3), the reaction solution was washed with saturated brine. After drying with anhydrous sodium sulfate, the solvent was distilled off under reduced pressure to obtain 791 mg of residue. This residue was then purified using silica gel column chromatography (elution solvent: hexane/ ethyl acetate=1/1) to obtain 313 mg of target compound (26-3). Yield: 70%

NMR (CDCl$_3$) δ: 1.43(9H,s), 1.7–2.2(2H,m), 2.3–2.5(4H, m), 3.10(2H,bt), 3.4–3.6(2H,m), 3.6–3.7(2H,m), 3.87(3H,s), 4.24(1H,s), 4.5–4.7(1H,m), 5.56(1H,bd), 7.1–7.3(6H,m), 7.3–7.5(4H,m), 7.74(1H,s)

(4) (S)-1-[2-(indol-2-yl)carbonylamino-4-(4-methoxycarbonyloxazol-5-yl)]butyryl-4-diphenylmethylpiperazine 2 ml of 4N hydrogen chloride (ethyl acetate solution) was added to 313 mg of the above-mentioned compound (26-3) followed by stirring for 1 hour at room temperature. After making the reaction solution alkaline by the addition of saturated sodium bicarbonate, the reaction solution was extracted with ethyl acetate (10 ml×3), washed with saturated brine and dried with anhydrous sodium sulfate. The solvent was distilled off under reduced pressure to obtain 219 mg of residue. The residue was dissolved in 4 ml of dichloromethane followed by the sequential addition of 84 mg of indole-2-carboxylic acid, 80 mg of 1-hydroxybenzotriazole hydrate and 100 mg of 1-ethyl-3-(3-dimethylaminopropyl)carbodiimide hydrochloride and stirring for 24 hours at room temperature. After concentrating the reaction solution, 10 ml of ethyl acetate was added. The reaction solution was then sequentially washed with 10% citric acid, saturated sodium bicarbonate and saturated brine, and dried with anhydrous sodium sulfate. The solvent was distilled off under reduced pressure to obtain 293 mg of residue. This residue was then purified with silica gel column chromatography (elution solvent: ethyl acetate) to obtain 268 mg of target compound (26-4). Yield: 79%

NMR (CDCl$_3$) δ: 1.9–2.4(6H,m), 3.0–3.3(2H,m), 3.45 (2H,bs), 3.64(2H,bs), 3.80(3H,s), 4.18(1H,s), 5.1–5.3(1H, m), 7.0–7.4(14H,m), 7.58(1H,d,J=7.9 Hz), 7.64(1H,s), 7.90 (1H,d,J=7.6 Hz,), 9.96(1H,bs)

(5) (S)-1-[4-(4-carboxyoxazol-5-yl)-2-(indol-2-yl) carbonylamino]butyryl-4-diphenylmethylpiperazine 268 mg of the above-mentioned compound (26-4) was dissolved in 3 ml of tetrahydrofuran followed by the sequential addition of 3 ml of water, 56 mg of lithium hydroxide hydrate and 2 ml of methanol and stirred for 1.5 hours at room temperature. After concentrating to roughly 4 ml, the reaction solution was neutralized by addition of 10% citric acid and extracted with dichloromethane. After washing with saturated brine, the reaction solution was dried with anhydrous sodium sulfate and the solvent was distilled off under reduced pressure to obtain 248 mg of target compound (26-5). Yield: 94%

IR (KBr) cm$^{-1}$: 1710, 1630, 1550, 1450

NMR (CDCl$_3$) δ: 1.9–2.5(6H,m), 2.9–3.8(6H,m), 4.13 (1H,s), 5.1–5.4(1H,m), 6.9–7.5(15H,m), 7.72(1H,s), 8.36 (1H,bd), 9.84(1H,bs)

Optical Rotation: $[\alpha]_D^{25}$=+7.9° (c=1.0, DMSO)

Example 27

(1) (S)-1-(3-benzyloxycarbonyl-2-t-butoxycarbonylamino) propionyl-4-diphenylmethylpiperazine 2.71 g of target compound (27-1) was obtained by following the same procedure as (1) of Example 26 from 1.62 g of β-benzyl N-t-butoxycarbonyl-L-aspartate. Yield: 97%

NMR (CDCl$_3$) δ: 1.39(9H,s), 2.2–2.4(4H,m), 2.62(1H,dd, J=15.9 Hz, 5.8 Hz), 2.82(1H,dd,J=15.9 Hz, 6.8 Hz), 3.4–3.7 (4H,m), 4.20(1H,s), 4.8–5.0(1H,m), 5.05(1H,d,J=14.9 Hz), 5.14(1H,d,J=14.9 Hz), 5.44(1H,bd), 7.1–7.4 (15H,m)

(2) (S)-1-(3-carboxy-2-t-butoxycarbonylamino)propionyl-4-diphenylmethylpiperazine 2.02 g of target compound (27-2) was obtained, by following the same procedure as (2) of Example 26, from 2.62 g of the above-mentioned compound (27-1). Yield: 92%

NMR (CDCl$_3$) δ: 1.39(9H,s), 2.2–2.5(4H,m), 2.55(1H,dd, J=15.8 Hz, 5.6 Hz), 2.76(1H,dd,J=15.8 Hz, 6.8 Hz), 3.4–3.8 (4H,m), 4.23(1H,s), 4.8–5.0(1H,m), 5.71(1H,bd), 7.1–7.3 (6H,m), 7.3–7.5(4H,m)

(3) (S)-4-diphenylmethyl-1-[3-(4-methoxycarbonyloxazol-5-yl)-2-t-butoxycarbonylamino]propionylpiperazine 536 mg of the target compound (27-3) was obtained, by following the same procedure as (3) of Example 26, from 934 mg of the above-mentioned compound (27-2). Yield: 49%

NMR (CDCl$_3$) δ: 1.34(9H,s), 2.3–2.5(4H,m), 3.2–3.4(2H, m), 3.5–3.7(4H,m), 3.89(3H,s), 4.26(1H,s), 4.8–5.0(1H,m), 5.50(1H,bd), 7.1–7.4(6H,m), 7.4–7.5(4H,m), 7.75 (1H,s)

(4) (S)-4-diphenylmethyl-1-[2-(indol-2-yl)carbonylamino-3-(4-methoxycarbonyloxazol-5-yl)]propionylpiperazine 489 mg of target compound (27-4) was obtained, by following the same procedure as (4) of Example 26, from mg of the above-mentioned compound (27-3). Yield: 87%

NMR (CDCl$_3$) δ: 2.3–2.5(4H,m), 3.4–3.8(6H,m), 3.77 (3H,s), 4.22(1H,s), 5.4–5.6(1H,m), 6.96(1H,s), 7.0–7.4 (13H,m), 7.51(1H,bd), 7.62(1H,d,J=7.6 Hz), 7.69(1H,s), 9.62 (1H,bs)

(5) (S)-1-[3-(4-carboxyoxazol-5-yl)-2-(indol-2-yl) carbonylamino]propionyl-4-diphenylmethylpiperazine 352 mg of target compound (27-5) was obtained, by following the same procedure as (5) of Example 26, from 412 mg of the above-mentioned compound (27-4). Yield: 87%

IR (KBr) cm$^{-1}$: 1720, 1630, 1540, 1450

NMR (DMSO-d$_6$) δ: 2.1–2.4(4H,m), 3.3–3.7(6H,m), 4.29 (1H,bs), 5.2–5.4(1H,m), 7.04(1H,dd,J=7.2 Hz, 7.2 Hz), 7.1–7.5(13H,m), 7.6(1H,d,J=7.8 Hz), 8.27(1H,s), 8.87(1H, d,J=8.2 Hz), 11.52(1H,s)

Optical Rotation: $[\alpha]_D^{25}$=−53.9° (c=1.2, DMSO)

Example 28

(1) (a): (S)-4-diphenylmethyl-1-[5-(5-methoxycarbonyl-1,2,3-triazol-1-yl)-2-t-butoxycarbonylamino]valerylpiperazine
(b): (S)-4-diphenylmethyl-1-[5-(4-methoxycarbonyl-1,2,3-triazol-1-yl)-2-t-butoxycarbonylamino]valerylpiperazine 274 mg of target compound (28-1)a and 902 mg of target compound (28-1)b were respectively obtained by following the same procedure of (4) of Example 23 and using 1.00 g of (S)-1-(5-azido-2-t-butoxycarbonylamino)valeryl-4-diphenylmethylpiperazine (compound (23-3) of Example 23), and methylpropiolate, instead of dimethyl acetylenedicarboxylate, as starting materials. Yield: 90% a: NMR (CDCl$_3$) δ: 1.42(9H,s), 1.5–1.6(4H,m), 2.2–2.5 (4H,m), 3.4–3.6(4H,m), 3.88(3H,s), 4.23(1H,s), 4.5–4.8(3H, m), 5.55(1H,bd), 7.1–7.5(11H,m), 8.10(1H,s)

b: NMR (CDCl$_3$) δ: 1.42(9H,s), 1.4–2.1(4H,m), 2.1–2.5 (4H,m), 3.3–3.7(4H,m), 3.94(3H,s), 4.20(1H,s), 4.3–4.5(2H, m), 4.5–4.7(1H,m), 5.12(1H,bd), 7.1–7.5(11H,m), 8.10(1H, d,J=2.0 Hz)

(2) (S)-4-diphenylmethyl-1-[2-(indol-2-yl)carbonylamino-5-(5-methoxycarbonyl-1,2,3-triazol-1-yl)valerylpiperazine 224 mg of target compound (28-2) was obtained by following the same procedure as (5) of Example 23 and using 244 mg of the above-mentioned compound (28-1)a as a starting material. Yield: 76%

NMR (CDCl$_3$) δ: 1.4–1.8(4H,m), 2.2–2.4(4H,m), 3.4–3.7 (4H,m), 3.80(3H,s), 4.21(1H,s), 4.6–4.8(2H,m), 5.1–5.2(1H, m), 7.0–7.5(14H,m), 7.5–7.8(2H,m), 8.09(1H,s), 9.9–10.0 (1H,m)

(3) (S)-1-[5-(5-carboxy-1,2,3-triazol-1-yl)-2-(indol-2-yl) carbonylamino]valeryl-4-diphenylmethylpiperazine 207 mg of target compound (28-3) was obtained by following the same procedure as (6) of Example 23 and using 224 mg of the above-mentioned compound (28-2) as a starting material. Yield: 95%

IR (KBr) cm$^{-1}$: 1630, 1540, 1450

NMR (CD$_3$OD) δ: 1.5–2.1(4H,m), 2.3–2.6(4H,m), 3.3–3.7(4H,m), 4.20(1H,s), 4.7–4.9(2H,m), 5.0–5.2(1H,m), 7.0–7.6(13H,m), 7.6–7.8(2H,m), 8.05(1H,s)

Optical Rotation: $[\alpha]_D^{25}$=+24.8° (c=0.8, DMSO)

Example 29

(1) (S)-4-diphenylmethyl-1-[2-(indol-2-yl)-5-(4-methoxycarbonyl-1,2,3-triazol-1-yl)]valerylpiperazine 582 mg of target compound (29-1) was obtained by following the same procedure as (5) of Example 23 and using 902 mg of (S)-4-diphenylmethyl-1-[5-(4-methoxycarbonyl-1,2,3-triazol-1-yl)-2-t-butoxycarbonylamino]valerylpiperazine (compound (28-1)b of Example 28) as a starting material. Yield: 60%

NMR (CDCl₃) δ: 1.6–2.1(4H,m), 2.4–2.5(4H,m), 3.4–3.7 (4H,m), 3.96(3H,s), 4.20(1H,s), 4.42(2H,t,J=13.7 Hz), 5.0–5.2(1H,m), 7.0–7.5(14H,m), 7.62(1H,d,J=8.5 Hz), 7.80 (1H,d,J=8.5 Hz), 8.21(1H,s)

(2) (S)-1-[5-(4-carboxy-1,2,3-triazol-1-yl)-2-(indol-2-yl) carboxyamino]valeryl-4-diphenylmethylpiperazine 427 mg of the target compound (29-2) was obtained by following the same procedure as (6) of Example 23 and using 486 mg of the above-mentioned compound (29-1) as a starting material. Yield: 90%

IR (KBr) cm⁻¹: 1630, 1550, 1450

NMR (CD₃OD) δ: 1.5–2.1(4H,m), 2.4–2.5(4H,m), 3.4–3.7(4H,m), 4.20(1H,s), 4.41(2H,t,J=13.2 Hz), 5.0–5.2 (1H,m), 7.0–7.4(13H,m), 7.62(1H,d,J=8.5 Hz), 7.77(1H,d, J=9.6 Hz), 8.15(1H,s)

Optical Rotation: [α]$_D^{25}$=+27.8° (c=1.0, DMSO)

Example 30

(1) (S)-1-(3-azido-2-t-butoxycarbonylamino)propionyl-4-diphenylmethylpiperazine 2.20 g of (S)-4-diphenylmethyl-1-(3-mesyloxy-2-t-butoxycarbonylamino)propionylpiperazine, as a starting material, was dissolved in 40 ml of dimethylformamide followed by the addition of 0.55 g of sodium azide and stirring for 1 hour at 80° C. The reaction solution was diluted with ethyl acetate, washed three times with water and dried with anhydrous sodium sulfate. The solvent was distilled off under reduced pressure to obtain 1.78 g of target compound (30-1). Yield: 84%

NMR (CDCl₃) δ: 1.44(9H,s), 2.40(4H,bs), 3.4–3.8(6H, m), 4.25(1H,s), 4.6–4.8(1H,m), 5.54(1H,bd), 7.1–7.5(10H, m)

(2) a: (S)-4-diphenylmethyl-1-[3-(4-methoxycarbonyl-1,2,3-triazol-1-yl)-2-t-butoxycarbonylamino]propionylpiperazine b: (S)-4-diphenylmethyl-1-[3-(5-methoxycarbonyl-1,2,3-triazol-1-yl)-2-t-butoxycarbonylamino]propionylpiperazine 1.50 g of the above-mentioned compound (30-1) was dissolved in 15 ml of 1,2-dichloroethane followed by the addition of 0.81 g of methyl propiolate and refluxing while heating for 4 hours. The solvent was distilled off under reduced pressure to obtain 1.91 g of residue. This was then purified using silica gel column chromatography (elution solvent: hexane/ethyl acetate=1/1) to obtain 1.05 g of target compound (30-2)a and 0.32 g of target compound (30-2)b. Yield: a: 60%, b: 18% a: NMR (CDCl₃) δ: 1.40(9H,s), 2.2–2.5(4H,m), 3.3–3.7 (4H,m), 3.95(3H,s), 4.23(1H,s), 4.5–4.7(2H,m), 4.9–5.1(1H, m), 5.53(1H,bd), 7.1–7.5(10H,m), 8.14(1H,s)

b: NMR (CDCl₃) δ: 1.26(9H,s), 2.3–2.6(4H,m), 3.5–3.8 (4H,m), 3.88(3H,s), 4.27(1H,s), 4.6–5.0(2H,m), 5.1–5.3(1H, m), 5.60(1H,bd), 7.1–7.5(10H,m), 8.07(1H,s)

(3) (S)-4-diphenylmethyl-1-[2-(indol-2-yl)carbonylamino-3-(4-methoxycarbonyl-1,2,3-triazol-1-yl)] propionylpiperazine 0.90 g of target compound (30-3) was obtained by following the same procedure as (5) of Example 23 and using 1.00 g of the above-mentioned compound (30-2)a as a starting material. Yield: 84%

NMR (CDCl₃) δ: 2.1–2.5(4H,m), 3.3–3.7(4H,m), 3.80 (3H,s), 4.16(1H,s), 4.78(2H,bs), 5.5–5.7(1H,m), 7.0–7.5 (14H,m), 7.70(1H,d,J=8.6 Hz), 7.90(1H,d,J=7.8 Hz), 8.24 (1H,s), 9.74(1H,s)

(4) (S)-1-[3-(4-carboxy-1,2,3-triazol-1-yl)-2-(indol-2-yl) carbonylamino]propionyl-4-diphenylmethylpiperazine 0.51 g of the target compound (30-4) was obtained by following the same procedure as (6) of Example 23 and using 0.90 g of the above-mentioned compound (30-3) as a starting material. Yield: 58%

IR (KBr) cm⁻¹: 1720, 1640, 1550, 1450

NMR (CD₃OD) δ: 2.1–2.5(4H,m), 3.4–3.8(4H,m), 4.19 (1H,s), 4.7–5.1(2H,m), 5.5–5.7(1H,m), 7.0–7.5(14H,m), 7.62(1H,d,J=8.2 Hz), 8.50(1H,s)

Optical Rotation: [α]$_D^{25}$=−64.8° (c=1.0, DMSO)

Example 31

(1) (S)-1-[3-(4,5-dimethoxycarbonyl-1,2,3-triazol-1-yl)-2-t-butoxycarbonylamino]propionyl-4-diphenylmethylpiperazine 2.01 g of target compound (31-1) was obtained by following the same procedure as (4) of Example 23 and using 2.00 g of (S)-1-(3-azido-2-t-butoxycarbonylamino) propionyl-4-diphenylmethylpiperazine as a starting material. Yield: 77%

NMR (CDCl₃) δ: 1.30(9H,s), 2.3–2.5(4H,m), 3.63(4H, bs), 3.95(3H,s), 3.98(3H,s),4.26(1H,s), 4.6–5.0(2H,m), 5.1–5.3(1H,m), 5.47(1H,bd), 7.1–7.5(10H,m)

(2) (S)-4-diphenylmethyl-1-[2-(indol-2-yl)carbonylamino-3-(4,5-dimethoxycarbonyl-1,2,3-triazol-1-yl)] propionylpiperazine 1.64 g of target compound (31-2) was obtained by following the same procedure as (5) of Example 23 and using 2.00 g of the above-mentioned compound (31-1) as a starting material. Yield: 76%

NMR (CDCl₃) δ: 2.2–2.6(4H,m), 3.4–3.7(4H,m), 3.73 (3H,s), 3.91(3H,s), 4.21(1H,s), 4.8–5.2(2H,m), 5.5–5.7(1H, m), 7.0–7.7(16H,m), 9.42(1H,s)

(3) (S)-1-[3-(4,5-dicarboxy-1,2,3-triazol-1-yl)-2-(indol-2-yl)carbonylamino]propionyl-4-diphenylmethylpiperazine 1.19 g of target compound (31-3) was obtained by following the same procedure as (6) of Example 23 and using 1.60 g of the above-mentioned compound (31-2) as a starting material. Yield: 78%

IR (KBr) cm⁻¹: 1720, 1640, 1540, 1490

NMR (CD₃OD) δ:2.40(4H,bs), 3.5–3.8(4H,m), 4.29(1H, s), 4.9–5.1 and 5.2–5.4(total 2H, m respectively), 5.7–5.9 (1H,m), 7.0–7.5(14H,m), 7.60(1H,d,J=8.4 Hz)

Optical Rotation: [α]$_D^{25}$=−108.6° (c=1.2, DMSO)

Example 32

(1) (S)-4-diphenylmethyl-1-[2-(indol-2-yl)carbonylamino-3-(5-methoxycarbonyl-1,2,3-triazol-1-yl)] propionylpiperazine 0.28 g of target compound (32-1) was obtained by following the same procedure as (5) of Example 23 and using (S)-4-diphenylmethyl-1-[3-(5-methoxycarbonyl-1,2,3-triazol-1-yl)-2-t-butoxycarbonylamino]propionylpiperazine (compound (30-2)b of Example 30) as a starting material. Yield: 80%

NMR (CDCl₃) δ: 2.42(4H,bs), 3.6–3.8(4H,m), 3.80(3H, s), 4.24(1H,s), 4.9–5.2(2H,m), 5.6–5.8(1H,m), 6.95(1H,bs), 7.0–7.5(14H,m), 7.63(1H,d,J=7.8 Hz), 8.05(1H,s), 9.22(1H, s)

(2) (S)-4-diphenylmethyl-1-[3-(5-carboxy-1,2,3-triazol-1-yl)-2-(indol-2-yl)carbonylamino]propionylpiperazine 0.22 g of target compound (32-2) was obtained by following the same procedure as (6) of Example 23 and using 0.28 g of the above-mentioned compound (32-1) as a starting material. Yield: 80%

IR (KBr) cm⁻¹: 1720, 1640, 1550, 1450

NMR (CD₃OD) δ: 2.58(4H,bs), 3.6–3.9(4H,m), 4.49(1H, s), 4.9–5.3(2H,m), 5.6–5.8(1H,m), 7.0–7.7(15H,m), 8.00 (1H,s)

Optical Rotation: $[\alpha]_D^{25}=-86.6°$ (c=0.9, DMSO)

The following indicates an experiment on the anti-CCK action of the compound of the present invention and a binding experiment.

Anti-cholecystokinin (CCK) Action in Extracted Guinea Pig Ileum

After sacrificing a male guinea pig (Hartley strain) by striking and exsanguination, a piece of extracted ileum was suspended from a Magnus tube, while applying tension of 0.5 g, containing 30 ml of Tyrode's solution (NaCl 136.9 mM, KCl 2.68 mM, $CaCl_2$ 1.8 mM, $MgCl_2$ 1.05 mM, $NaH_2PO_4$ 0.42 mM, $NaHCO_3$ 11.9 mM and glucose 5.55 mM) and ventilated with mixed $O_2$ gas containing 5% $CO_2$ at 37° C. Changes in contraction were recorded on smoked paper for isotonicity via a bevel.

The piece of ileum was allowed to stand undisturbed for 30 minutes and then contracted by addition $1×10^{-8}M$ CCK-8. After washing, this was repeated several times. After the contraction by CCK-8 had stabilized, the test compound was added. Contraction resulting from addition of $1×10^{-8}M$ CCK was then measured 5 minutes later. The contraction caused by CCK-8 and the contraction caused by CCK-8 in the presence of the test compound at varying concentrations were compared, and the resulting IC50 values (concentration of test substance at which contraction caused by CCK-8 is inhibited by 50%) are shown in Table 2.

The compound numbers shown in Table 2 indicate the target compounds according to the numbers of the embodiments.

TABLE 2

Anti-CCK Action in Extracted Guinea Pig Ileum

| Compound Number | Active IC50 (µM) |
|---|---|
| CR1505 | 3.3 |
| 1-6 | 0.013 |
| 2-6 | 0.06 |
| 6-2 | 0.052 |
| 8-5 | 0.35 |
| 10-4 | 0.048 |
| 12-2 | 0.027 |
| 14-5 | 0.26 |
| 15-4 | 0.12 |
| 17-3 | 0.0072 |
| 22-4 | 0.036 |
| 24-3 | 0.12 |
| 26-5 | 0.017 |
| 27-5 | 0.19 |
| 31-3 | 0.032 |
| 32-2 | 0.036 |

Peripheral Receptor (CCK-A) and Central Receptor (CCK-B) Binding Experiment

Preparation of CCK receptor standard and a [$^3$H]-CCK-8 binding inhibition experiment were conducted in accordance with van Dijik et al. (The Journal of Neuroscience, Vol. 4, pp. 1021–1033, 1984).

The pancreas and cerebrum of male rats (Japan Laboratory Animals), which were sacrificed by decapitation and having body weights of 250–300 g, were extracted and immersed in cold Hepes buffer. After suspending these tissues using a Potter homogenizer, the suspension was centrifuged for 10 minutes at 48,000×g. The resulting residue was again suspended by addition of cold Hepes buffer and centrifuged for 10 minutes at 48,000×g. The resulting residue was transferred to cold incubation buffer.

A 1 ml aliquot of the homogenate was incubated for 60 minutes at 25° C. in the presence of 0.2 nM [$^3$H]-CCK-8 and the test compound, in the presence of vehicle only (for measurement of 100% binding), or in the presence of 1 µM cold CCK-8 (for measurement of non-specific binding). Next, the reaction solution was promptly suction filtered using a Whatman glass GF/B filter immersed in Hepes buffer followed by washing the filter with cold Hepes buffer. Next, the glass filter was placed in Aquasol-2 followed by assay of radioactivity with a liquid scintillation counter.

The amount of specific binding to CCK receptors was determined from the difference between the amount of 100% binding and the amount of non-specific binding, while $IC_{50}$ values were calculated from the inhibition rate of specific binding by the test compound. Those results are shown in Table 3.

The compound numbers shown in Table 3 indicate the target compounds according to the number of the embodiment.

TABLE 3

| Compound Number | $IC_{50}$ (µM) CCK-A | $IC_{50}$ (µM) CCK-B | CCK-B/ CCK-A |
|---|---|---|---|
| CR1505 | 1.5 | 24 | 16 |
| 1-6 | 0.0051 | 14 | 2745 |
| 2-6 | 0.0043 | 57 | 13256 |
| 6-2 | 0.043 | 18 | 419 |
| 7-4 | 0.8 | 61 | 76 |
| 8-5 | 0.05 | 57 | 1140 |
| 9-3 | 0.21 | 6 | 29 |
| 10-4 | 0.006 | 36 | 6000 |
| 12-2 | 0.005 | 42 | 8400 |
| 14-5 | 0.17 | 100 | 588 |
| 15-4 | 0.03 | 8.8 | 293 |
| 17-3 | 0.56 | 13 | 23 |
| 19-5 | 0.009 | 64 | 7111 |
| 20-2 | 0.06 | >1000 | >16667 |
| 21-2 | 0.013 | 1700 | 130770 |
| 22-4 | 0.02 | 56 | 2800 |
| 23-6 | 0.14 | 25 | 179 |
| 24-3 | 0.037 | 69 | 1865 |
| 25-7 | 0.21 | 12 | 57 |
| 26-5 | 0.016 | 10 | 625 |
| 27-5 | 0.18 | 9.6 | 53 |
| 28-3 | 0.07 | 3 | 43 |
| 29-2 | 1.5 | 26 | 17 |

EFFECT OF THE INVENTION

The compounds of the present invention exhibit powerful anti-CCK activity in vitro on the nanomol order ($10^{-9}M$). Namely, as is shown in the experimental examples of Table 2, the $IC_{50}$ value of the compound of the present invention with respect to the extracted guinea pig ileum (in vitro) of Table 2 was $7.2×10^{-9}M$ (compound 17). In addition, as is similarly shown in the experimental examples of Table 3 of the present invention, in a binding experiment on CCK-A receptors prepared from the cell membranes of rat pancreas, the compounds of the present invention demonstrated powerful activity in the manner of $5.1×10^{-9}M$ (compound 1), $4.3×10^{-9}M$ (compound 2), $5.0×10^{-9}M$ (compound 12), $6.0×10^{-9}M$ (compound 10) and $9.0×10^{-9}M$ (compound 19). Namely, the compounds of the present invention exhibited strong activity roughly 165–350 times stronger than CR1505 in the binding experiment.

In addition, these compounds exhibit relatively weak binding with CCK-B receptors originating in the cell membrane of rat brain cells, exhibiting a high degree of selectivity that is roughly 20–130000 times greater than for CCK-A receptors.

Thus, the compounds of the present invention are useful in the prevention and treatment of pancreatic cancer, gastric ulcer, duodenal ulcer, digestive ulcer, colitis, gall bladder dysfunction and particularly acute pancreatitis.

We claim:

1. A compound represented by the following formula:

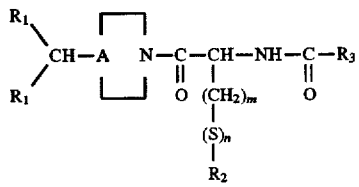

wherein, m is an integer of 1 to 3;

n is an integer 0 or 1;

A represents CH or N atom, and forms, together with the N atom bonded to the carbonyl group, a piperidine ring or a piperazine ring;

$R_1$ independently represents a straight or branched chain alkyl group having 1 to 4 carbon atoms; a cycloalkyl group having 3 to 8 carbon atoms; a phenyl group, unsubstituted or substituted with a halogen atom or with an alkoxy group having 1 to 4 carbon atoms; or a pyridyl group; or two $R_1$, together with the group >CH— to which they bind, form a dibenzo[a,d] cycloheptenyl group or a fluorenyl group;

$R_2$ represents a phenyl group substituted with a carboxyl or a methyl-substituted carboxyl group; a pyridyl group substituted with a carboxyl or carboxyl group substituted with a methyl, ethyl or methoxy carboxyl methyl group, a pyrazinyl group substituted with a carboxyl or methyl-substituted carboxyl group, an oxazolyl substituted with a carboxyl or methyl-substituted carboxyl group, a triazolyl substituted with one or two carboxyl or methyl-substituted, carboxyl groups, or a phosphonopyridyl group; and $R_3$ represents an indolyl group unsubstituted or substituted with a substituent selected from the group consisting of a halogen atom, a hydroxy group, an alkoxy group having 1 to 4 carbon atoms and methoxycarbonyl ethyl group or the pharmaceutically acceptable salts thereof.

2. A compound as set forth in claim 1 wherein $R_1$ is a phenyl group substituted with a fluorine atom or methoxy group.

3. A compound as set forth in claim 1 wherein $R_3$ is an indolyl group substituted by a group selected from the group consisting of a chlorine atom, a hydroxy group and a methoxy group.

4. A compound as set forth in claim 1 that is (R)-1-[3-(3-carboxypyridin-2-yl)thio-2-(indol-2-yl)carbonylamino] propionyl-4-diphenylmethylpiperazine.

5. A compound as set forth in claim 1 that is (R)-1-[3-(3-carboxypyridin-2-yl)thio-2-(indol-2-yl)carbonylamino] propionyl-4-diphenylmethylpiperidine.

6. A compound as set forth in claim 1 that is (R)-1-[3-(3-carboxypyridin-2-yl)thio-2-(5-chloroindol-2-yl) carbonylamino]propionyl-4-diphenylmethylpiperidine.

7. A compound as set forth in claim 1 that is (R)-1-[3-(3-carboxypyridin-2-yl)thio-2-(5-methoxyindol-2-yl) carbonylamino]propionyl-4-diphenylmethylpiperidine.

8. A method for prevention or treatment of gall bladder, dysfunctional or acute pancreatitis by selectively inhibiting cholecystokin A receptors by a method for selectively inhibitory-effective amount of a compound of the formula:

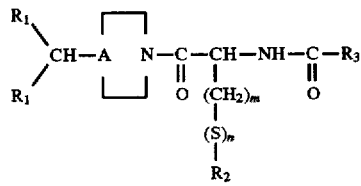

wherein, m is an integer of 1 to 3;

n is an integer 0 or 1;

A represents CH or N atom, and forms, together with the N atom bonded to the carbonyl group, a piperidine ring or a piperazine ring;

$R_1$ independently represents a straight or branched chain alkyl group having 1 to 4 carbon atoms; a cycloalkyl group having 3 to 8 carbon atoms; a phenyl group, unsubstituted or substituted with a halogen atom or with an alkoxy group having 1 to 4 carbon atoms; or a pyridyl group;

$R_2$ represents a phenyl group substituted with a carboxyl or a methyl-substituted carboxyl group; a pyridyl group substituted with a carboxyl or methyl-substituted carboxyl group, a pyrazinyl group substituted with a carboxyl or methyl-substituted carboxyl groups; an oxazoyl group substituted with a carboxyl or methyl-substututed carboxyl group; a triazolyl substituted with one or two carboxyl or methyl-substituted carboxyl groups or a phosphonopyridyl group; and $R_3$ represents an indolyl group unsubstituted or substituted with a substitutent selected from the group consisting of a halogen atom, a hydroxy group; an alkoxy group having 1 to 4 carbon atoms and methoxylcarbonyl ethyl group and the pharmaceutically acceptable salts thereof.

9. A method according to claim 8 wherein said compound is (R)-1-[3-(3-carboxypyridin-2-yl)thio-2-(indol-2-yl) carbonylamino]propionyl-4-diphenylmethylpiperazine.

10. A method according to claim 8 wherein said compound is (R)-1-[3-(3-carboxypyridin-2-yl)thio-2-(indol-2-yl)carbonylamino]propionyl-4-diphenylmethylpiperazine.

11. A method according to claim 8 wherein said compound is (R)-1-[3-carboxypyridin-2-yl)thio 2-(5-chloroindol-2-yl)carbonylamino]propionyl-4-diphenylmethylpiperidine.

12. A method according to claim 8 wherein said compound is (R)-1-{3-(3carbonypyridin-2-yl}thio-2-(5methoxyindol-2-yl)carboxylamino propionyl-4-diphenylmethylpiperidine.

* * * * *